United States Patent
Eriguchi et al.

(10) Patent No.: US 11,298,080 B2
(45) Date of Patent: Apr. 12, 2022

(54) REPRODUCTION TERMINAL AND REPRODUCTION METHOD

(71) Applicants: Sony Mobile Communications Inc., Tokyo (JP); Sony Corporation, Tokyo (JP)

(72) Inventors: Masao Eriguchi, Tokyo (JP); Kaneo Todoroki, Kanagawa (JP); Ikuo Yamano, Tokyo (JP)

(73) Assignees: SONY MOBILE COMMUNICATIONS INC., Tokyo (JP); SONY CORPORATION, Tokyo (JP)

( * ) Notice: Subject to any disclaimer, the term of this patent is extended or adjusted under 35 U.S.C. 154(b) by 507 days.

(21) Appl. No.: 16/339,005

(22) PCT Filed: Nov. 2, 2017

(86) PCT No.: PCT/JP2017/039684
§ 371 (c)(1),
(2) Date: Apr. 3, 2019

(87) PCT Pub. No.: WO2018/088319
PCT Pub. Date: May 17, 2018

(65) Prior Publication Data
US 2019/0223798 A1      Jul. 25, 2019

(30) Foreign Application Priority Data
Nov. 11, 2016   (JP) .............................. JP2016-220425

(51) Int. Cl.
*A61B 5/02*   (2006.01)
*G10L 15/22*  (2006.01)
(Continued)

(52) U.S. Cl.
CPC .............. *A61B 5/6813* (2013.01); *A61B 5/02* (2013.01); *A61B 5/02433* (2013.01);
(Continued)

(58) Field of Classification Search
CPC ....... A61B 5/6813; A61B 5/6802; A61B 5/00; A61B 5/681; A61B 5/486; A61B 5/375;
(Continued)

(56) References Cited

U.S. PATENT DOCUMENTS 6,415,257 B1 *  7/2002  Junqua .................... G10L 17/00
704/275
2002/0019584 A1   2/2002  Schulze et al.
(Continued)

FOREIGN PATENT DOCUMENTS

EP       3041200 A1    7/2016
JP     2001-357191 A  12/2001
(Continued)

OTHER PUBLICATIONS

European Search Repod dated Aug. 28, 2019, issued in corresponding European Application No. 17870232.0, 8 pages.
(Continued)

*Primary Examiner* — Huyen X Vo
(74) *Attorney, Agent, or Firm* — Xsensus LLP

(57) ABSTRACT

[Object] To provide a reproduction apparatus and a reproduction method which enable easier operation of providing a response to distributed information.
[Solution] A reproduction terminal including: a reproducing unit configured to reproduce distributed information; a sensor unit configured to detect body action of a user; and a control unit configured to process operation regarding provision of a response to the distributed information on the basis of the body action detected at the sensor unit.

17 Claims, 24 Drawing Sheets

(51) Int. Cl.
  *A61B 5/00* (2006.01)
  *G06F 3/01* (2006.01)
  *G06F 13/00* (2006.01)
  *A61B 5/024* (2006.01)
  *G06F 13/14* (2006.01)

(52) U.S. Cl.
  CPC .............. *A61B 5/486* (2013.01); *A61B 5/681* (2013.01); *G06F 3/01* (2013.01); *G06F 3/016* (2013.01); *G06F 13/00* (2013.01); *G06F 13/14* (2013.01); *G10L 15/22* (2013.01); *G06F 3/011* (2013.01); *G10L 2015/223* (2013.01)

(58) Field of Classification Search
  CPC ....... A61B 5/02433; A61B 5/024; A61B 5/02;
    A61B 5/468; G06F 13/14; G06F 13/00;
    G06F 15/16; G06F 9/46; G06F 3/01;
    G06F 3/16; G06F 3/016; G06F 3/011;
    G06F 3/167; G06F 1/163; G06F 1/16;
    G10L 15/22; G10L 2015/223; A61F 4/00;
    G09B 21/00; G10H 1/344; H03K 17/94;
    H04H 60/33; H04H 60/63
  See application file for complete search history.

(56) References Cited

U.S. PATENT DOCUMENTS

| | | | |
|---|---|---|---|
| 2003/0159567 A1* | 8/2003 | Subotnick | G06F 3/04883 84/626 |
| 2007/0097073 A1 | 5/2007 | Takashima et al. | |
| 2008/0059578 A1* | 3/2008 | Albertson | G06F 3/017 709/204 |
| 2010/0215170 A1* | 8/2010 | Kannappan | H04M 1/2535 379/418 |
| 2011/0298829 A1* | 12/2011 | Stafford | G06K 9/00248 345/659 |
| 2013/0033971 A1 | 2/2013 | Stier | |
| 2013/0307771 A1* | 11/2013 | Parker | G06F 3/0482 345/158 |
| 2014/0052751 A1* | 2/2014 | Zhang | G06F 16/436 707/769 |
| 2014/0161412 A1* | 6/2014 | Chase | H04R 1/028 386/224 |
| 2015/0293597 A1* | 10/2015 | Mishra | G06F 3/013 715/810 |
| 2016/0269510 A1 | 9/2016 | Sasaki et al. | |
| 2016/0330258 A1 | 11/2016 | Sandhu | |
| 2017/0048286 A1* | 2/2017 | Ichihashi | H04N 7/15 |
| 2017/0238812 A1* | 8/2017 | Atlas | A61B 5/0205 |

FOREIGN PATENT DOCUMENTS

| | | |
|---|---|---|
| JP | 2003-240582 A | 8/2003 |
| JP | 2007-122501 A | 5/2007 |
| JP | 2014-6076 A | 1/2014 |
| JP | 2014-147030 A | 8/2014 |
| JP | 2015-106223 A | 6/2015 |
| WO | 2015/029573 A1 | 3/2015 |

OTHER PUBLICATIONS

International Search Report dated Jan. 30, 2018 for PCT/JP2017/039684 filed on Nov. 2, 2017, 9 pages including English Translation.

* cited by examiner

FIG. 12
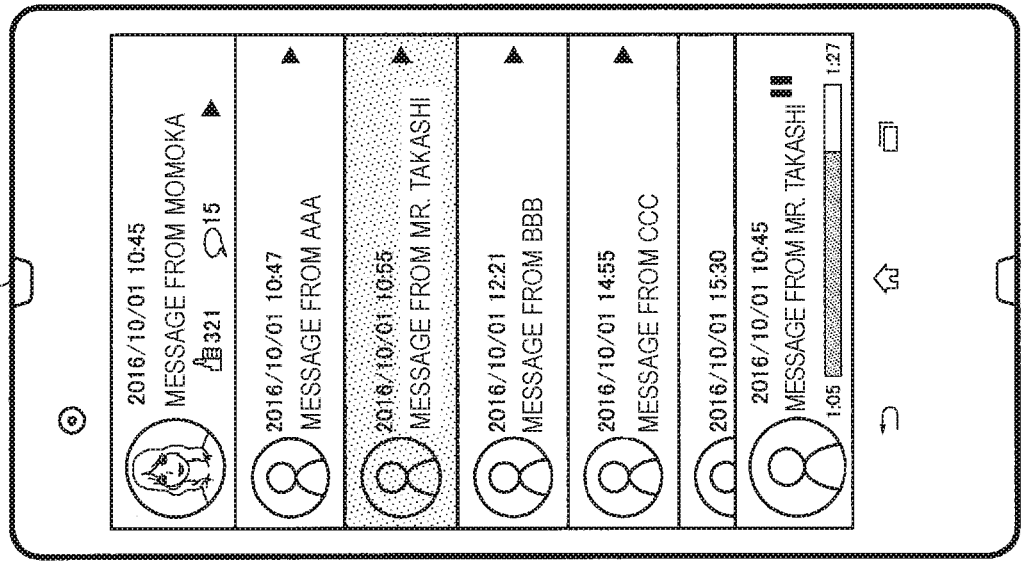
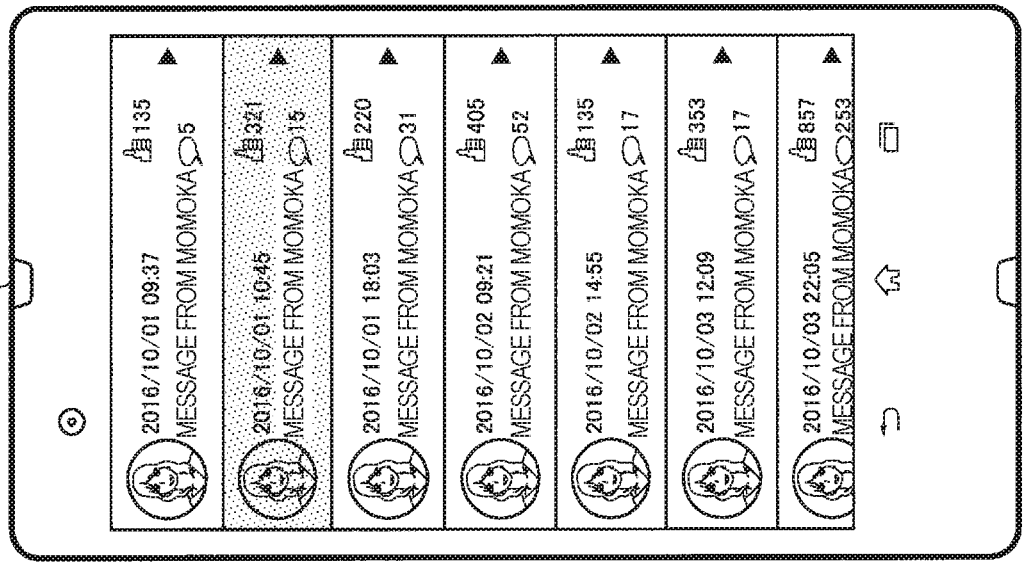

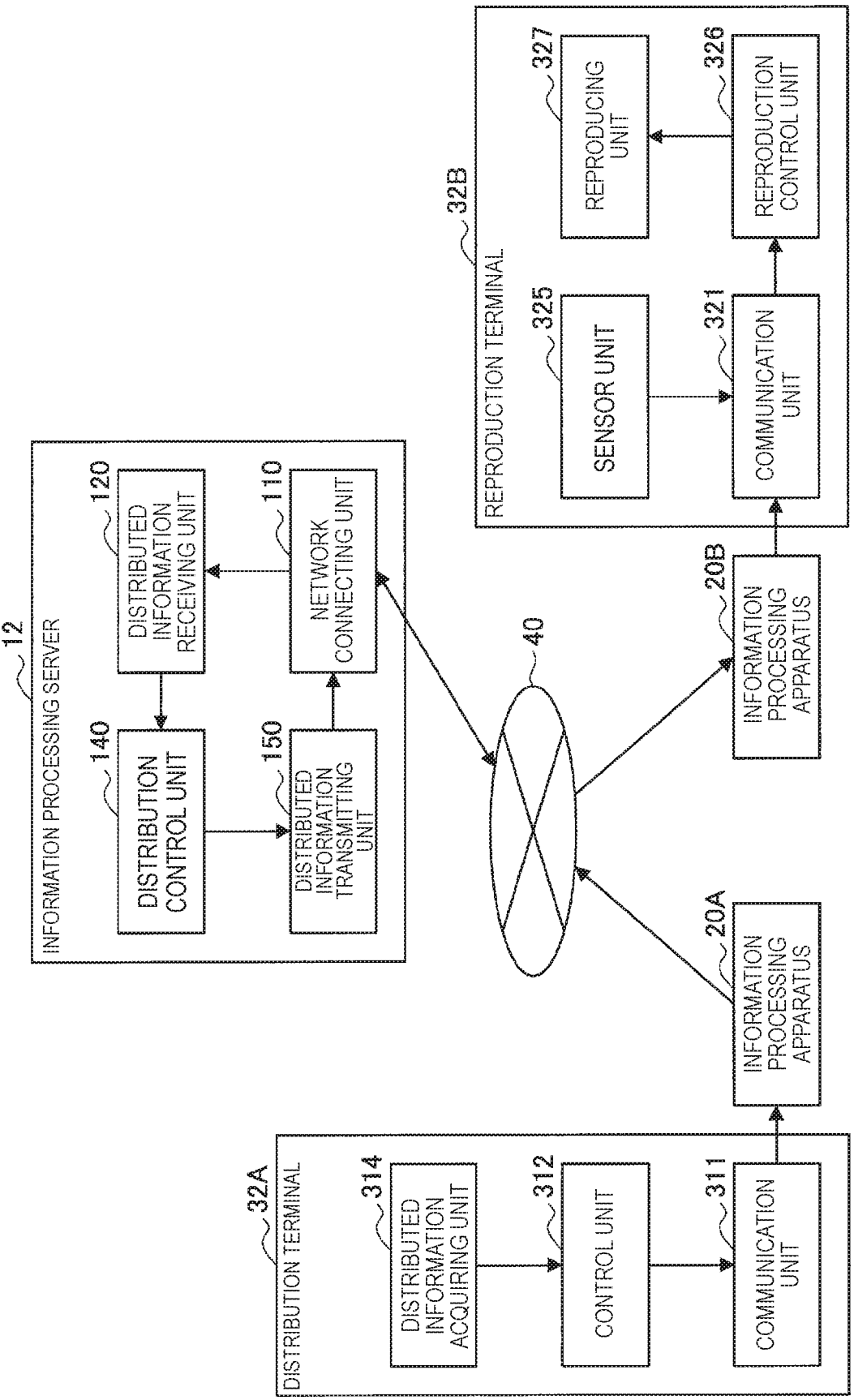

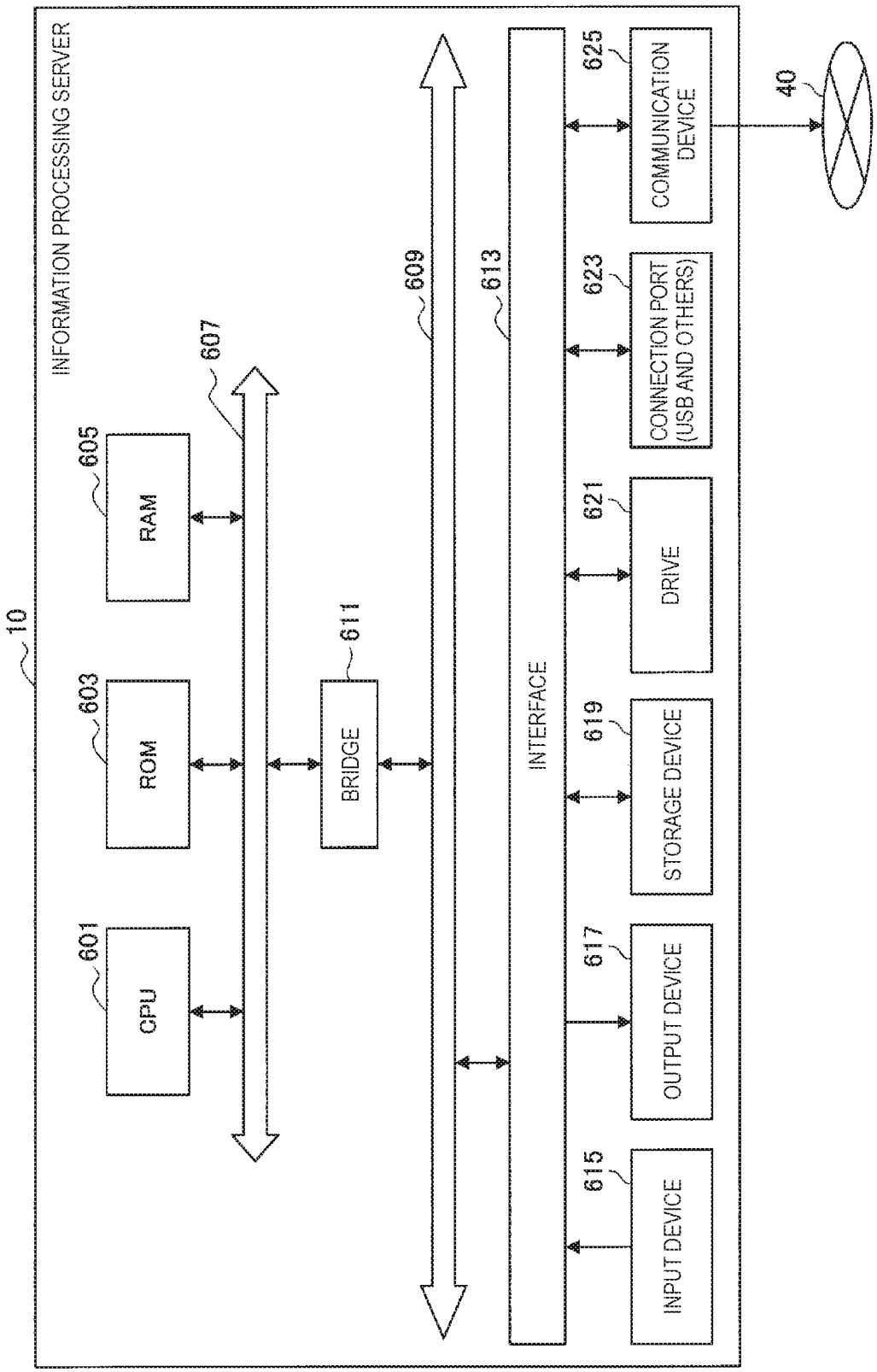

REPRODUCTION TERMINAL AND REPRODUCTION METHOD

CROSS-REFERENCE TO RELATED APPLICATIONS

The present application is based on PCT filing PCT/JP2017/039684, filed Nov. 2, 2017 which claims priority to JP 2016-220425, filed Nov. 11, 2016, the entire contents of each are incorporated herein by reference.

TECHNICAL FIELD

The present disclosure relates to a reproduction terminal and a reproduction method.

BACKGROUND ART

In recent years, service which distributes information to many and unspecified targets via a network such as the Internet and a mobile communication network is widely offered. Further, in such service, reaction, or the like, to the distributed information can be returned from the targets.

For example, the following Patent Literature 1 discloses a reaction survey method in which a commercial message is distributed to viewers from a broadcast station and degrees of reaction to the distributed commercial message are collected from the viewers via content for data broadcasting, or the like.

CITATION LIST

Patent Literature

Patent Literature 1: JP 2001-357191A

DISCLOSURE OF INVENTION

Technical Problem

However, with the method disclosed in Patent Literature 1 described above, the distributed information is a commercial message such as edited image information, and does not strongly stimulate sensitivity or image of the viewers. Therefore, to effectively utilize bi-directionality and instantaneousness of the Internet, or the like, it is desired to efficiently obtain responses to the distributed information.

The present disclosure proposes a reproduction terminal and a reproduction method which enable easier operation of providing a response to distributed information.

Solution to Problem

According to the present disclosure, there is provided a reproduction terminal including: a reproducing unit configured to reproduce distributed information; a sensor unit configured to detect body action of a user; and a control unit configured to process operation regarding provision of a response to the distributed information on the basis of the body action detected at the sensor unit.

In addition, according to the present disclosure, there is provided a reproduction method including: reproducing distributed information; detecting body action of a user; and processing operation regarding provision of a response to the distributed information on the basis of the detected body action by an arithmetic processing unit.

According to the present disclosure, the user can perform operation of providing the response to the distributed information through the body action.

Advantageous Effects of Invention

According to the present disclosure as described above, a user can easily perform operation of providing a response to distributed information.

Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 12 is an explanatory diagram illustrating an example of display in which the distributed information is associated with comments to the distributed information.

FIG. 16 is a block diagram explaining a specific configuration of the information processing system according to the second embodiment.

FIG. 24 is a block diagram illustrating an example of a hardware configuration of the information processing server according to each embodiment of the present disclosure.

MODE(S) FOR CARRYING OUT THE INVENTION

Figure 1:
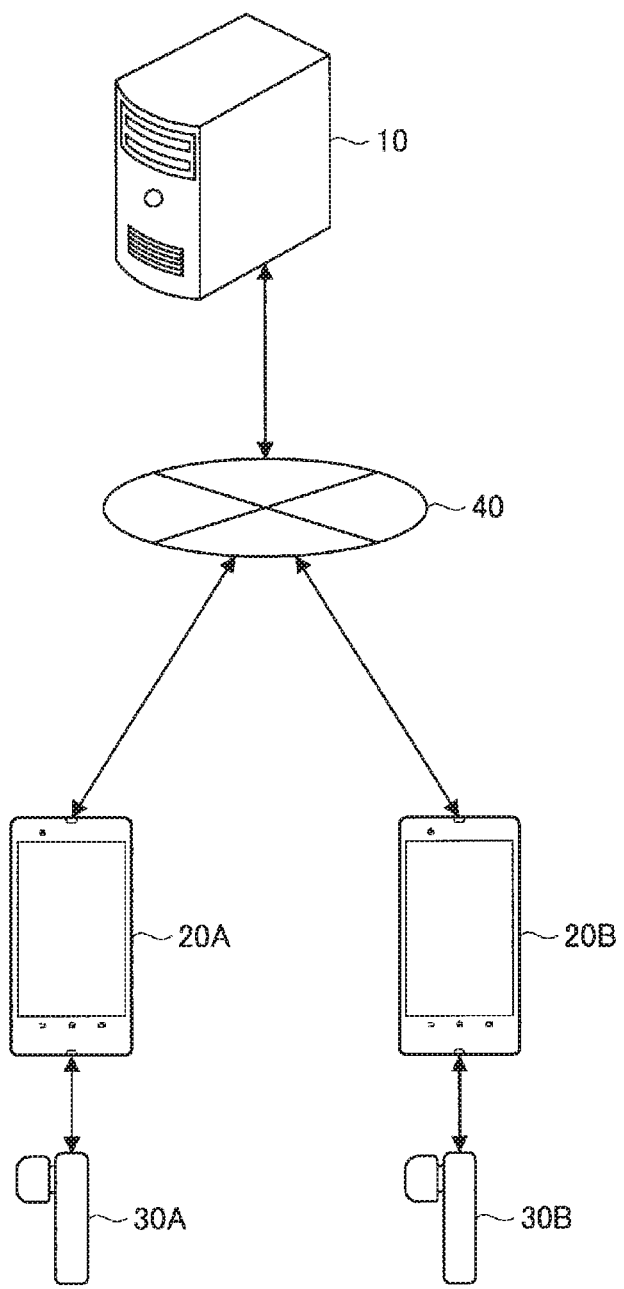
FIG. 1 is an explanatory diagram explaining outline of an information processing system according to a first embodiment of the present disclosure.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

Note that description will be provided in the following order.
1. First embodiment
1.1. Outline of information processing system
1.2. Configuration of information processing system
1.3. Operation of information processing system
1.4. Modified examples
2. Second embodiment
2.1. Outline of information processing system
2.2. Configuration of information processing system
2.3. Operation of information processing system
2.4. Modified examples
3. Hardware configuration of information processing server
4. Conclusion

1. First Embodiment

[1.1. Outline of Information Processing System]

First, outline of an information processing system according to a first embodiment of the present disclosure will be described with reference to FIG. 1. FIG. 1 is an explanatory diagram explaining the outline of the information processing system according to the first embodiment of the present disclosure.

The information processing system according to the present embodiment is an information distribution system which receives distributed information from a distributer and transmits the distributed information to a user. Further, in the information processing system according to the present embodiment, it is also possible to feed back a response such as a comment and evaluation to the distributed information from the user to the distributor. Note that the distributor is, for example, an idol, celebrity, an opinion leader, or the like, and the user is, for example, a fan, a follower, or the like, of the distributor.

In the present embodiment, the distributed information may be, for example, distributed information depending on physicality of the distributor or may be voice information uttered by the distributor. Because the voice information has a frequency spectrum different depending on a vocal cord of the distributor who has uttered the voice information, the voice information is information which is characteristic of the distributor and which has stronger concreteness. Therefore, in the information processing system according to the present embodiment, by the voice uttered by the distributor being distributed as the distributed information, it is possible to cause the user to whom the distributed information is distributed to have a stronger feeling.

As illustrated in FIG. 1, the information processing system according to the present embodiment includes a distribution terminal 30A and an information processing apparatus 20A possessed by the distributor, a reproduction terminal 30B and an information processing apparatus 20B possessed by the user who receives the distributed information, and an information processing server 10 connected to the information processing apparatuses 20A and 20B via a network 40.

The distribution terminal 30A and the reproduction terminal 30B are, for example, information processing apparatuses worn on any portion of the body of the distributor or the user. The distribution terminal 30A has at least a sound collecting function, and the reproduction terminal 30B has at least a voice reproducing function.

Specifically, the distribution terminal 30A acquires voice uttered by the distributor using the sound collecting function. The sound collecting function may be realized with, for example, a sound collecting device such as a microphone which collects surrounding sound and a signal processing circuit such as a digital signal processor (DSP). Further, the reproduction terminal 30B reproduces voice information included in the distributed information using the voice reproducing function. The voice reproducing function may be realized with a voice output device such as a speaker and a headphone and a signal processing circuit such as an amplifier.

In the information processing system according to the present embodiment, the voice uttered by the distributor is collected at the distribution terminal 30A as the distributed information, and the distributed information is distributed to the reproduction terminal 30B via the network 40. By this means, the user can reproduce the distributed information at the reproduction terminal 30B and can listen to the voice uttered by the distributor.

The distribution terminal 30A and the reproduction terminal 30B may have any form, and may be, for example, spectacle-type terminals worn on the face of the user, wristwatch-type terminals worn on the wrist, or the like, of the user, headset-type terminals worn on the head of the user, earphone-type terminals inserted into the ears of the user, or the like. However, because the distributed information distributed in the present embodiment is voice information, the distribution terminal 30A and the reproduction terminal 30B may be earphone-type terminals as illustrated in FIG. 1.

Note that the distribution terminal 30A and the reproduction terminal 30B transmit/receive the distributed information to/from the information processing server 10 via the information processing apparatuses 20A and 20B. However, the distribution terminal 30A and the reproduction terminal 30B may directly transmit/receive the distributed information to/from the information processing server 10 without intervening the information processing apparatuses 20A and 20B.

The information processing apparatus 20A and the information processing apparatus 20B are communication apparatuses possessed by the distributor or the user, and have a function for performing communication with the distribution terminal 30A or the reproduction terminal 30B and a function for connecting to the network 40. The information processing apparatus 20A and the information processing apparatus 20B may be, for example, a smartphone, a mobile phone, a tablet terminal, a personal digital assistant (PDA), or the like.

Specifically, the information processing apparatus 20A receives the voice information (that is, the distributed information) collected at the distribution terminal 30A using the function for performing communication with the distribution terminal 30A, and transmits the voice information to the information processing server 10 using the function for connecting to the network 40. Meanwhile, the information processing apparatus 20B receives the voice information (that is, the distributed information) from the information processing server 10 using the function for connecting to the network 40 and transmits the voice information to the reproduction terminal 30B using the function for performing communication with the reproduction terminal 30B.

The function for performing communication between the information processing apparatus 20A and the information processing apparatus 20B, and the distribution terminal 30A and the reproduction terminal 30B may be realized with, for example, an antenna and a communication circuit which wirelessly communicate information in a distance from several meters to approximately 100 meters, and, specifically, may be realized with an antenna and a communication circuit which support Bluetooth (registered trademark), or the like. Further, the function for connecting the information processing apparatus 20A and the information processing apparatus 20B, and the network 40 may be realized with an antenna and a communication circuit which support connection to a wireless LAN, a public switched telephone network, a mobile communication network or the Internet.

The network 40 is a communication network in which information is transmitted and received. The network 40 may be, for example, a local area network (LAN), a wide area network (WAN), the Internet, a satellite communication network, a telephone network, a mobile communication network (such as, for example, a 3G or 4G network) or an internet protocol-virtual private network (IP-VPN), or the like.

The information processing server 10 receives the distributed information from the distribution terminal 30A and controls transmission of the distributed information to the reproduction terminal 30B on the basis of whether the user wears the reproduction terminal 30B.

Specifically, in the case where the user wears the reproduction terminal 30B upon receipt of the distributed information, the information processing server 10 transmits the distributed information to the reproduction terminal 30B. Meanwhile, in the case where the user does not wear the reproduction terminal 30B upon receipt of the distributed information, the information processing server 10 does not transmit the distributed information to the reproduction terminal 30B and transmits the distributed information to the reproduction terminal 30B in the case where the user wears the reproduction terminal 30B thereafter. Note that whether the user wears the reproduction terminal 30B can be detected by, for example, various kinds of sensors provided at the reproduction terminal 30B. Specifically, a proximity sensor which detects approach of an object, a touch sensor which detects touch with an object, an acceleration sensor which detects an attitude and orientation of the reproduction terminal 30B, or the like, are provided at the reproduction terminal 30B, and the reproduction terminal 30B may judge whether or not the reproduction terminal 30B is worn on the user on the basis of information from these sensors.

The distributed information is information which depends on physicality of the distributor, which is characteristic of the distributor and which has strong concreteness. Therefore, the information processing server 10 tries to cause the user to directly listen to the distributed information by controlling transmission of the distributed information so that the distributed information is reproduced in a state where the user wears the reproduction terminal 30B. By this means, the information processing server 10 can cause the user to have a stronger feeling.

Further, the information processing server 10 may store responses such as comments and evaluation from the user to the distributed information in association with the distributed information. Further, the information processing server 10 may convey these responses from the user to the distributed information to the distributor who distributes the distributed information. According to this, because the information processing server 10 can cause bi-directional communication between the distributor and the user via the distributed information, it is possible to activate interaction between the distributor and the user. Particularly, in the information processing system according to the present embodiment, because the distributed information is information depending on physicality of the distributor, it can be expected that more active interaction may occur.

Therefore, according to the information processing system according to the present embodiment, it is possible to distribute the distributed information such as voice information which depends on physicality of the distributor to the user more effectively.

Note that, while, in FIG. 1, an example has been described where the information processing system includes the distribution terminal 30A, the information processing apparatus 20A, the information processing server 10, the information processing apparatus 20B and the reproduction terminal 30B, the technology according to the present disclosure is not limited to such an example. For example, the distribution terminal 30A and the information processing apparatus 20A may be one integrated information processing apparatus, and the reproduction terminal 30B and the information processing apparatus 20B may be one integrated information processing apparatus. Further, part or all of the functions of the information processing server 10 may be executed at one of the information processing apparatus 20A and the information processing apparatus 20B. Still further, for example, part or all of the information stored in a distributed information storage unit 130 of the information processing server 10 which will be described later may be stored in at least one of the information processing apparatus 20A or the information processing apparatus 20B.

[1.2. Configuration of Information Processing System]

Figure 2A:
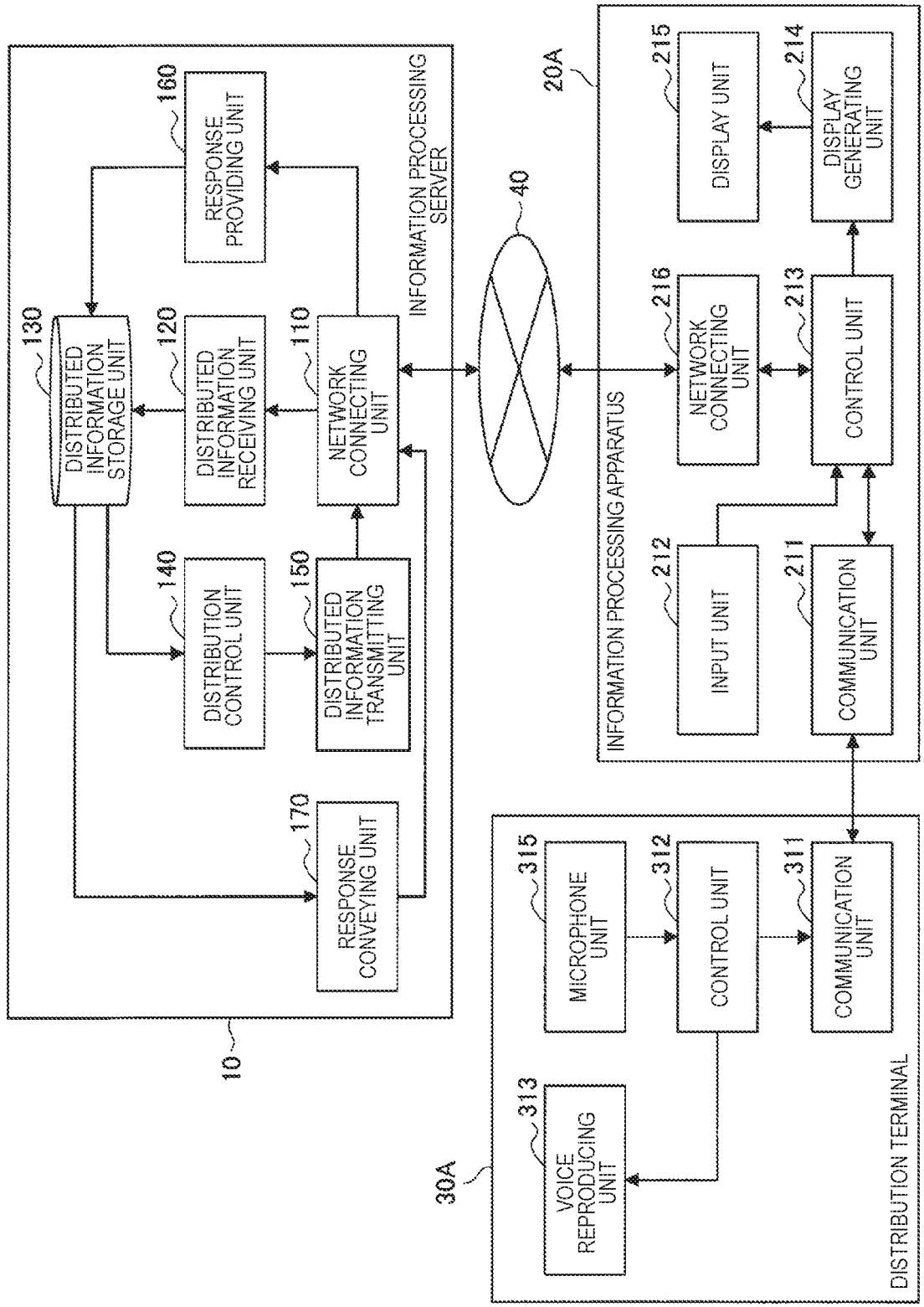
FIG. 2A is a block diagram explaining specific configurations of an information processing server, an information processing apparatus and a distribution terminal in the information processing system according to the first embodiment.

A configuration of the information processing system according to the present embodiment will be described next with reference to FIG. 2A and FIG. 2B. FIG. 2A is a block diagram explaining specific configurations of the information processing server 10, the information processing apparatus 20A and the distribution terminal 30A in the information processing system according to the present embodiment, and FIG. 2B is a block diagram explaining specific configurations of the information processing server 10, the information processing apparatus 20B and the reproduction terminal 30B in the information processing system according to the present embodiment.

Figure 2B:
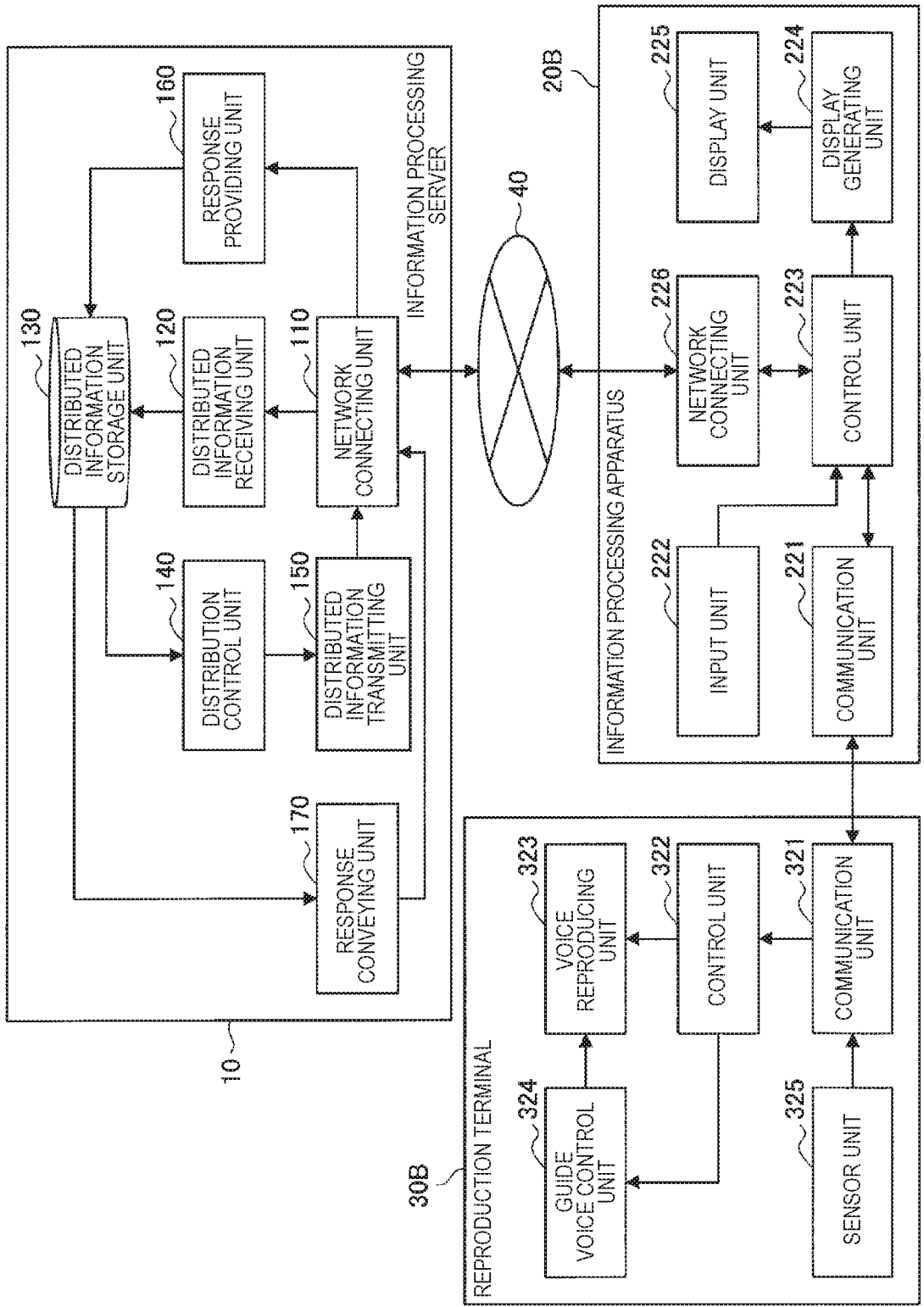
FIG. 2B is a block diagram explaining specific configurations of an information processing server, an information processing apparatus and a reproduction terminal in the information processing system according to the first embodiment.

As illustrated in FIG. 2A and FIG. 2B, the distribution terminal 30A includes a microphone unit 315, a voice reproducing unit 313, a control unit 312 and a communication unit 311, and the information processing apparatus 20A includes an input unit 212, a communication unit 211, a control unit 213, a display generating unit 214, a display unit 215 and a network connecting unit 216.

Further, the information processing server 10 includes a network connecting unit 110, a distributed information receiving unit 120, a distributed information storage unit 130, a distribution control unit 140, a distributed information transmitting unit 150, a response providing unit 160 and a response conveying unit 170.

Still further, the reproduction terminal 30B includes a sensor unit 325, a control unit 322, a communication unit 321, a guide voice control unit 324 and a voice reproducing unit 323, and the information processing apparatus 20B includes an input unit 222, a communication unit 221, a control unit 223, a display generating unit 224, a display unit 225 and a network connecting unit 226.

(Distribution Terminal 30A)

The microphone unit 315 includes, for example, a sound collecting device such as a microphone, and a signal processing circuit such as a DSP, and collects sound around the distribution terminal 30A. Specifically, the microphone unit 315 may collect voice uttered by the distributor who wears the distribution terminal 30A and may generate voice information to be used as the distributed information.

The voice reproducing unit 313 includes, for example, a voice output device such as a speaker and a headphone, and a signal processing circuit such as an amplifier, and reproduces the voice information as voice. Specifically, the voice reproducing unit 313 may reproduce the voice information collected by the microphone unit 315 to cause the distributor to confirm the voice uttered by the distributor, or may reproduce a response such as a comment provided to the distributed information by the user as the voice information.

The control unit 312 includes, for example, a micro processing unit (MPU) which is an arithmetic processing unit, and a memory in which a control program, a control parameter, or the like, are stored, and controls each component of the distribution terminal 30A. Specifically, the control unit 312 controls each component so that the voice information collected by the microphone unit 315 is transmitted to the information processing apparatus 20A as the distributed information. Further, the control unit 312 may control each component so that a response such as a comment provided to the distributed information from the user, from the information processing apparatus 20A.

The communication unit 311 includes, for example, an antenna and a communication circuit, and transmits/receives information to/from the information processing apparatus 20A. Specifically, the communication unit 311 may transmit/receive the distributed information and information regarding a response to the distributed information from the user, or the like, to/from the communication unit 211 of the information processing apparatus 20A.

A scheme of communication performed by the communication unit 311 may be, for example, a short-distance communication scheme having a communication possible range with a radius from several meters to approximately 100 meters, and, specifically, may be Wi-Fi (registered trademark), ZigBee (registered trademark), Bluetooth (registered trademark), Bluetooth Low Energy (registered trademark), ANT (registered trademark), ANT+ (registered trademark), or the like. However, the scheme of communication performed by the communication unit 311 is not limited to the above, and may be, for example, mobile communication such as 3G, 4G and long term evolution (LTE).

(Information Processing Apparatus 20A)

The communication unit 211 includes, for example, an antenna and a communication circuit of a communication scheme which is the same as that of the communication unit 311 of the above-described distribution terminal 30A, and transmits/receives information to/from the distribution terminal 30A. Specifically, the communication unit 211 may transmit/receive the distributed information, and information regarding a response to the distributed information from the user, or the like, to/from the communication unit 311 of the distribution terminal 30A.

The communication scheme of the communication unit 211 is the same as that of the communication unit 311 of the above-described distribution terminal 30A, and may be, for example, Wi-Fi (registered trademark), ZigBee (registered trademark), Bluetooth (registered trademark), Bluetooth Low Energy (registered trademark), ANT (registered trademark), ANT+ (registered trademark), or the like, and may be mobile communication such as 3G, 4G and LTE.

The input unit 212 may include an input device such as a touch panel, a keyboard, a button, a microphone, a switch and a lever, to which information is input, an input control circuit which generates an input signal on the basis of input of the user and outputs the input signal to the control unit 213, or the like.

The control unit 213 includes a central processing unit (CPU) which is an arithmetic processing unit, a read only memory (ROM) in which a control program, a control parameter, or the like, are stored, and a random access memory (RAM) in which a program to be used upon operation, a parameter which changes as appropriate, or the like, are temporarily stored, and controls each component of the information processing apparatus 20A.

The display generating unit 214 generates display to be presented to the distributor at the display unit 215. For example, the display generating unit 214 may generate display which is a list of the distributed information generated at the distribution terminal 30A, and which is to be presented to the distributor. Further, the display generating unit 214 may generate display which presents the distributed information and a response to the distributed information in association with each other for each piece of the distributed information.

The display unit 215 presents an image, or the like, to the distributor on the basis of the display generated by the display generating unit 214. The display unit 215 may include a display apparatus such as a liquid crystal display (LCD) apparatus, an organic electroluminescence display (OLED) apparatus and a lamp.

The network connecting unit 216 includes, for example, an interface for connecting to the network 40 and a communication circuit, and transmits/receives information to/from the information processing server 10 via the network 40. Specifically, the network connecting unit 216 transmits the voice information collected at the distribution terminal 30A to the information processing server 10 as the distributed information. Further, the network connecting unit 216 may receive a response such as a comment and evaluation from the user to the transmitted distributed information from the information processing server 10.

The network connecting unit 216 may include, for example, an interface and a communication circuit which can be connected to a LAN, a WAN, the Internet, a satellite communication network, a telephone network, a mobile communication network, IP-VPN, or the like, and may include an interface and a communication circuit which can be connected to a mobile communication network such as 3G, 4G and LTE.

(Information Processing Server 10)

The network connecting unit 110 includes, for example, an interface for connecting to the network 40 and a communication circuit, and transmits/receives information to/from the information processing apparatus 20A and the information processing apparatus 20B via the network 40. For example, like the network connecting units 216 and 226, the network connecting unit 110 may include an interface and a communication circuit which can be connected to a LAN, a WAN, the Internet, a satellite communication network, a telephone network, a mobile communication network, IP-VPN, or the like.

The distributed information receiving unit 120 receives the distributed information generated at the distribution terminal 30A via the information processing apparatus 20A. The distributed information is information which depends on physicality of the distributor, and which is voice information generated by using the microphone unit 315, or the like, of the distribution terminal 30A. The information processing server 10 can activate interaction between the distributor and the user by distributing the distributed information distributed from the distributor to the user.

The distributed information storage unit 130 stores the distributed information distributed from the distributor. Specifically, in the case where the user does not wear the reproduction terminal 30B upon receipt of the distributed information by the distributed information receiving unit 120, the distributed information storage unit 130 temporarily stores the distributed information which has not been distributed to the reproduction terminal 30B. Further, the distributed information storage unit 130 may store each piece of the distributed information transmitted to the reproduction terminal 30B. In such a case, the distributed information storage unit 130 can store each piece of the distributed information and a response to the distributed information from the user in association with each other.

The distribution control unit 140 controls transmission of the distributed information to the reproduction terminal 30B on the basis of whether the user wears the reproduction terminal 30B. Specifically, in the case where the user wears the reproduction terminal 30B, the distribution control unit 140 controls a timing for transmitting the distributed information so that the distributed information is reproduced at the reproduction terminal 30B. Therefore, in the case where the user does not wear the reproduction terminal 30B, the distribution control unit 140 suspends transmission of the distributed information to the reproduction terminal 30B and transmits the distributed information to the reproduction terminal 30B at a time point at which it is confirmed that the reproduction terminal 30B is worn. By this means, because the distribution control unit 140 can cause the user to directly listen to the distributed information, it is possible to cause the user who listens to the voice uttered by the distributor as the distributed information to have a strong feeling.

The distributed information transmitting unit 150 transmits the distributed information to the reproduction terminal 30B on the basis of control by the distribution control unit 140. Specifically, in the case where the user wears the reproduction terminal 30B, the distributed information transmitting unit 150 instantaneously transmits the distributed information received at the distributed information receiving unit 120 to the reproduction terminal 30B. By this means, because the distributed information transmitting unit 150 can cause the user to listen to the distributed information received from the distributor in real time, it is possible to strengthen a special feeling that time is shared between the distributor and the user. Further, for the distributed information distributed from the distributor in the case where the user does not wear the reproduction terminal 30B, the distributed information transmitting unit 150 transmits the distributed information to the reproduction terminal 30B in the case where it can be confirmed that the user wears the reproduction terminal 30B. By this means, the distributed information transmitting unit 150 can cause the user to reliably listen to the distributed information using the reproduction terminal 30B.

The response providing unit 160 associates the comment, the evaluation, or the like, to the distributed information from the user with the distributed information. Specifically, the response providing unit 160 receives a comment or feedback provided to the distributed information from the user who has listened to the distributed information and associates the comment or the feedback with the distributed information. Further, the response providing unit 160 counts the number of points indicating evaluation, approval, favorite, or the like, provided to the distributed information from respective users and associates the counted number of points with the distributed information. By this means, the response providing unit 160 can associate content and a degree of reaction to the distributed information from the users for each piece of the distributed information.

The response conveying unit 170 conveys a response such as a comment and reaction to the distributed information from the user to the distributor. Specifically, the response conveying unit 170 conveys the response such as the comment and the evaluation associated with the distributed information by the response providing unit 160 to the distributor who has distributed the distributed information. For example, the response conveying unit 170 transmits the comment or the feedback provided to the distributed information to the information processing apparatus 20A or the distribution terminal 30A of the distributor who has transmitted the distributed information. Further, the response conveying unit 170 transmits the number of points provided to the distributed information from the respective users to the information processing apparatus 20A or the distribution terminal 30A of the distributor who has transmitted the distributed information. By this means, the distributor can easily confirm reaction of the users to the distributed information distributed from the distributor with the information processing apparatus 20A or the distribution terminal 30A at hand.

(Information Processing Apparatus 20B)

The network connecting unit 226 includes, for example, an interface for connecting to the network 40 and a communication circuit, and transmits/receives information to/from the information processing server 10 via the network 40. Specifically, the network connecting unit 226 receives the voice information to be reproduced at the reproduction terminal 30B from the information processing server 10 as the distributed information. Further, the network connecting unit 226 may transmit the response such as the comment and the evaluation to the distributed information from the user to the information processing server 10.

The network connecting unit 226 may include, for example, an interface and a communication circuit which can be connected to a LAN, a WAN, the Internet, a satellite communication network, a telephone network, a mobile communication network, IP-VPN, or the like, and may include an interface and a communication circuit which can be connected to a mobile communication network such as 3G, 4G and LTE.

The input unit 222 may include an input device such as a touch panel, a keyboard, a button, a microphone, a switch and a lever, to which information is input, an input control circuit which generates an input signal on the basis of input of the user and outputs the input signal to the control unit 223, or the like.

The control unit 223 includes a CPU which is an arithmetic processing unit, a ROM in which a control program, a control parameter, or the like, are stored, and a RAM in which a program to be used upon operation, a parameter which changes as appropriate, or the like, are temporarily stored, and controls each component of the information processing apparatus 20B.

The display generating unit 224 generates display to be presented to the user at the display unit 225. For example, the display generating unit 224 may generate display which is a list of the distributed information reproduced at the reproduction terminal 30B, and which is to be presented to the user.

The display unit 225 presents an image, or the like, to the user on the basis of the display generated by the display generating unit 224. The display unit 225 may include a display apparatus such as an LCD apparatus, an OLED apparatus and a lamp.

The communication unit 221 includes, for example, an antenna and a communication circuit of a communication scheme which is the same as that of the communication unit 321 of the reproduction terminal 30B, and transmits/receives information to/from the reproduction terminal 30B. Specifically, the communication unit 221 may transmit/receive the distributed information, and information regarding a response to the distributed information from the user, or the like, to/from the communication unit 321 of the reproduction terminal 30B.

The communication scheme of the communication unit 221 is the same as that of the communication unit 321 of the reproduction terminal 30B, and may be, for example, Wi-Fi (registered trademark), ZigBee (registered trademark), Bluetooth (registered trademark), Bluetooth Low Energy (registered trademark), ANT (registered trademark), ANT+ (registered trademark), or the like, and may be mobile communication such as 3G, 4G and LTE.

(Reproduction Terminal 30B)

The communication unit 321 includes, for example, an antenna and a communication circuit, and transmits/receives information to/from the information processing apparatus 20B. Specifically, the communication unit 321 may transmit/receive the distributed information and information regarding a response to the distributed information from the user, or the like, to/from the communication unit 221 of the information processing apparatus 20B.

A scheme of communication performed by the communication unit 321 may be, for example, a short-distance communication scheme having a communication possible range with a radius from several meters to approximately 100 meters, and, specifically, may be Wi-Fi (registered trademark), ZigBee (registered trademark), Bluetooth (registered trademark), Bluetooth Low Energy (registered trademark), ANT (registered trademark), ANT+ (registered trademark), or the like. However, the scheme of communication performed by the communication unit 321 is not limited to the above, and may be, for example, mobile communication such as 3G, 4G and LTE.

The sensor unit 325 is various kinds of sensors mounted on the reproduction terminal 30B. The sensor unit 325 includes at least a sensor which acquires information to be used in the case where it is judged whether or not the reproduction terminal 30B is worn on the user. For example, the sensor unit 325 may include a proximity sensor which detects approach of an object to the reproduction terminal 30B, a touch sensor which detects touch between the reproduction terminal 30B and an object, an acceleration sensor which detects an attitude and orientation of the reproduction terminal 30B, or the like, and may judge whether or not the reproduction terminal 30B is worn on the user through information from these sensors.

Further, the sensor unit 325 may include a microphone which collects voice of the user, and may include an acceleration sensor, a gyro sensor or a vibration sensor which detects gesture of the user. According to such a sensor unit 325, the user can intuitively perform input to the reproduction terminal 30B without intervening an input device such as a touch panel, a keyboard, a button, a microphone, a switch and a lever.

The control unit 322 includes, for example, an MPU which is an arithmetic processing unit, and a memory in which a control program, a control parameter, or the like, are stored, and controls each component of the reproduction terminal 30B. Specifically, the control unit 322 controls each component so as to reproduce the distributed information received from the information processing apparatus 20B. Further, the control unit 322 may control each component so as to transmit the voice information such as a comment from the user input from the sensor unit 325 to the information processing apparatus 20B.

The guide voice control unit 324 controls output of the voice information which guides the user in operation of the reproduction terminal 30B. For example, in the case where the reproduction terminal 30B is a headset-type terminal or an earphone-type terminal which does not include a display unit, the reproduction terminal 30B cannot instruct the user on an operation method through an image, or the like. Therefore, at the reproduction terminal 30B, the guide voice control unit 324 causes the voice information to be reproduced at the voice reproducing unit 323, and the reproduction terminal 30B instructs the user how to operate the reproduction terminal 30B through voice. By this means, at the reproduction terminal 30B, it is possible to improve operability for the user.

Further, the voice information which guides the user in operation of the reproduction terminal 30B may be voice information of voice which is uttered by the distributor and collected. These kinds of voice may be prepared in advance by the utterance of the distributor being collected. Further, in the case where there is a plurality of distributors, the user may arbitrarily designate a distributor whose uttered voice is to be used to guide the user in operation of the reproduction terminal 30B.

The voice reproducing unit 323 includes, for example, a voice output device such as a speaker and a headphone, and a signal processing circuit such as an amplifier, and reproduces the voice information as voice. Specifically, the voice reproducing unit 323 may reproduce the distributed information which is the voice information transmitted from the information processing server 10. Further, the voice reproducing unit 323 may guide the user in operation of the reproduction terminal 30B by reproducing the voice information on the basis of control by the guide voice control unit 324.

[1.3. Operation of Information Processing System]

Subsequently, operation of the information processing system according to the present embodiment will be described using specific examples with reference to FIG. 3 to FIG. 13.

(Operation on Reproduction Terminal Side)

Figure 3:
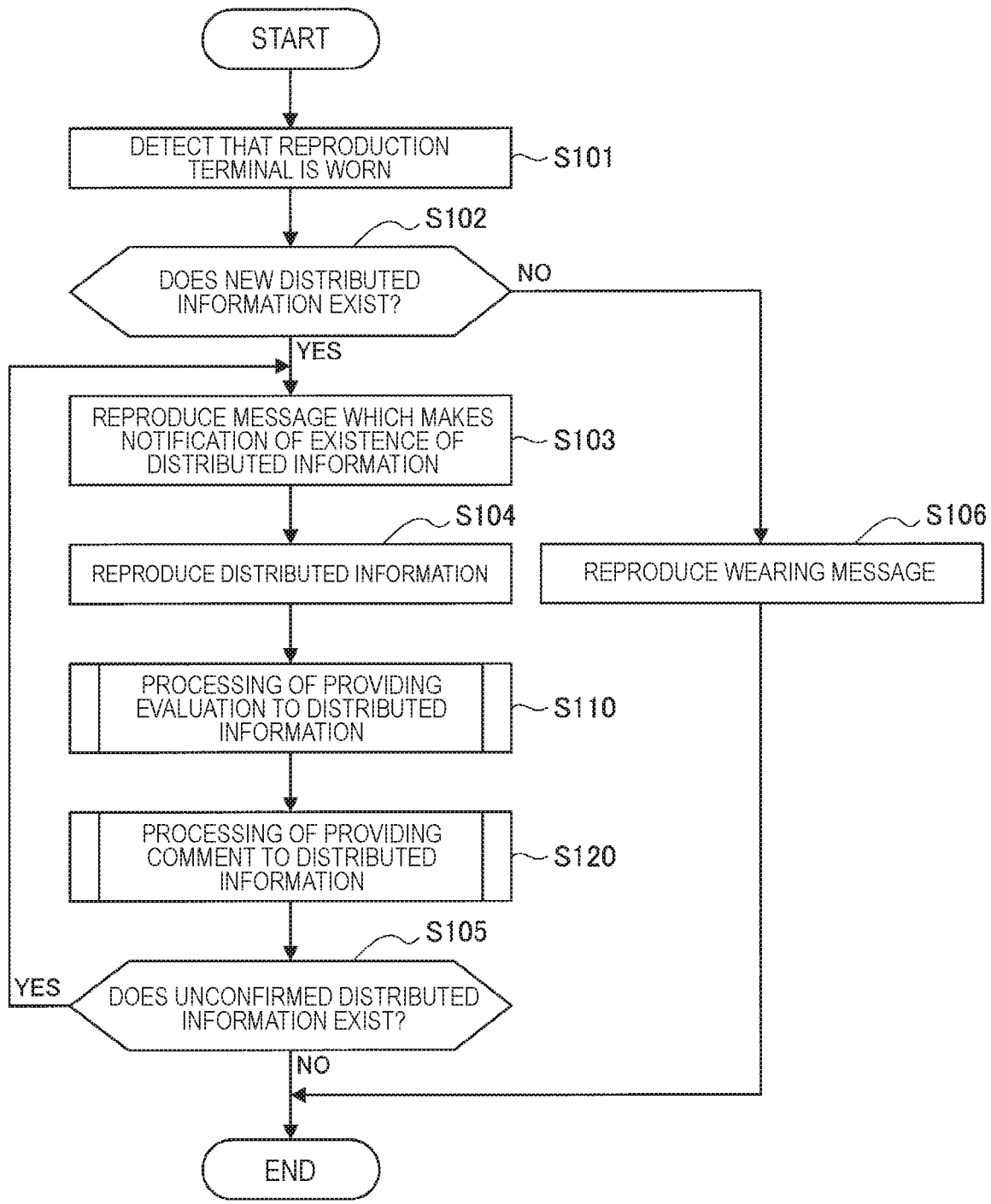
FIG. 3 is a flowchart explaining operation on the reproduction terminal side of the information processing system according to the first embodiment.
Figure 4:
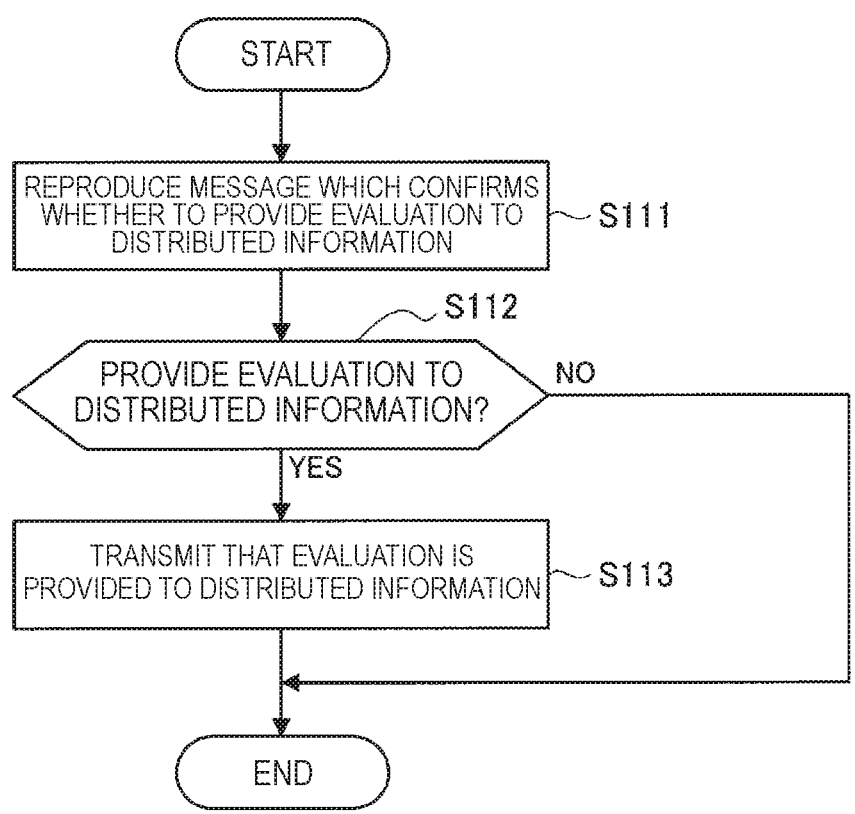
FIG. 4 is a flowchart explaining specific operation of "processing of providing evaluation" in FIG. 3.
Figure 5:
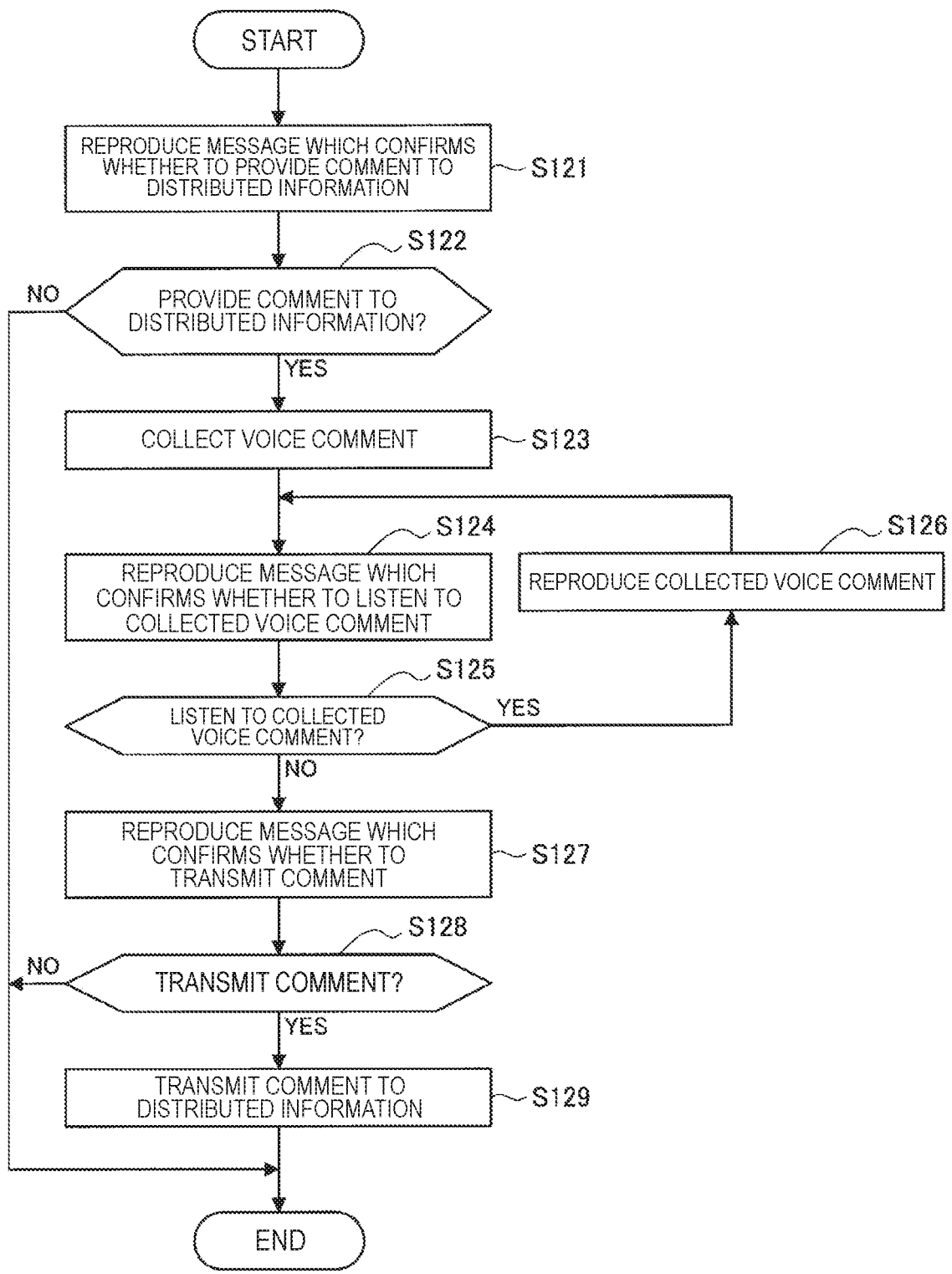
FIG. 5 is a flowchart explaining specific operation of "processing of providing a comment" in FIG. 3.

First, operation on the reproduction terminal 30B side of the information processing system according to the present embodiment will be described with reference to FIG. 3 to FIG. 5. FIG. 3 is a flowchart explaining the operation on the reproduction terminal 30B side of the information processing system according to the present embodiment. FIG. 4 is a flowchart explaining specific operation of "processing of providing evaluation" in FIG. 3, and FIG. 5 is a flowchart explaining specific operation of "processing of providing a comment" in FIG. 3.

As illustrated in FIG. 3, in the information processing system according to the present embodiment, in the case where the user listens to the distributed information, first, it is detected by the sensor unit 325 that the reproduction terminal 30B is worn on the user (S101). Then, it is confirmed whether or not there exists distributed information which has not been listened to by the user (S102). In the case where there is no distributed information which has not been listened to (S102: No), a predetermined wearing message which is reproduced upon wearing is reproduced (S106). Note that whether or not there exists distributed information which has not been listened to can be confirmed by an inquiry being made to the distribution control unit 140 of the information processing server 10 as to whether or not there is distributed information which has not been listened to from, for example, the control unit 322 of the reproduction terminal 30B or the control unit 223 of the information processing apparatus 20B via the network 40.

The predetermined wearing message is voice information which is stored in the reproduction terminal 30B, or the like, in advance. The predetermined wearing message may be voice information which is voice uttered by the distributor and collected in advance, or may be, for example, greeting by the distributor, reading of time or date by the distributor, a predetermined message by the distributor (for example, a signature phrase of the distributor), or the like. Further, the predetermined wearing message may be changed as appropriate. Specifically, the predetermined wearing message may be changed in accordance with a time slot, date and day of week at which the reproduction terminal 30B is worn, may be changed in accordance with history of wearing of the reproduction terminal 30B (such as, for example, an elapsed time period since date and time at which the reproduction terminal 30B has been worn last time), or may be randomly changed. For example, content of the predetermined message may be controlled to be normally greeting from the distributor in accordance with a time slot and day of week at which the reproduction terminal 30B is worn and to be a signature phrase of the distributor at a low probability.

In the case where there exists distributed information which has not been listened to (S102: Yes), a message which makes a notification of existence of the distributed information is reproduced (S103). The message which makes a notification of existence of the distributed information may be the voice information stored in the reproduction terminal 30B, or the like, in advance and may be the voice information uttered by the distributor in a similar manner to the predetermined wearing message. Further, the message which makes a notification of existence of the distributed information may be changed in accordance with the number of pieces of the distributed information which has not been listened to.

Here, in addition to the above-described predetermined wearing message and the message which makes a notification of existence of the distributed information, voice (also referred to as guide voice) to be reproduced to indicate a state of the reproduction terminal 30B or guide the user in operation, or the like, may be voice of the distributor. Further, in the case where there is a plurality of distributors, the guide voice may be, for example, voice of a distributor which is randomly selected from the plurality of distributors or may be voice of a distributor (for example, the user's favorite distributor) designated by the user.

In the case where there is a plurality of distributors, and voice of the distributor designated by the user is guide voice, the distributor who utters the guide voice may be temporarily changed so as to be different from the distributor who has uttered the distributed information. In such a case, the reproduction terminal 30B can notify the user of existence of the distributed information through guide voice with natural content which introduces from another distributor that distributed information is distributed from one distributor. Note that, while the distributor who utters the guide voice which makes a notification of existence of the distributed information may be the same as the distributor who has uttered the distributed information, in such a case, the reproduction terminal 30B may notify the user of existence of the distributed information through guide voice with content which makes a notification from the distributor himself/herself.

Note that the predetermined wearing message may be, for example, stored in the information processing server 10. For example, in the case where it is detected by the sensor unit 325 that the reproduction terminal 30B is worn on the user, the reproduction terminal 30B may transmit information which notifies the information processing server 10 that the reproduction terminal 30B is worn on the user via the network 40. By this means, by the information processing server 10 which receives the information transmitting the predetermined wearing message to the reproduction terminal 30B, the reproduction terminal 30B can reproduce the predetermined wearing message. Further, the above-described message which makes a notification of existence of the distributed information and the guide voice may be also stored in the information processing server 10 in a similar manner. For example, the reproduction terminal 30B requests the information processing server 10 for these messages or the guide voice via the network 40 at a timing at which these messages or the guide voice are reproduced, and receives these messages or the guide voice from the information processing server 10. According to this, the reproduction terminal 30B can reproduce the message which makes a notification of the distributed information and the guide voice, received from the information processing server 10.

Then, the transmitted distributed information is reproduced (S104). By this means, the distributed information is listened to by the user.

Subsequently, processing of providing evaluation to the distributed information which has been listened to is performed (S110). The processing of providing evaluation to the distributed information will be described with reference to FIG. 4. Specifically, as illustrated in FIG. 4, first, guide voice which confirms whether or not evaluation is provided to the distributed information which has been listened to is reproduced (S111).

Note that the guide voice which confirms whether or not evaluation is provided may include description regarding input operation for selecting each of a case where evaluation is provided and a case where evaluation is not provided. Further, in the case where input operation regarding whether or not evaluation is provided is performed by the user during reproduction of this guide voice, remaining reproduction of the guide voice may be skipped.

Here, the evaluation indicates agreement, evaluation, approval, favorite, affection, or the like, to the distributed information and can be provided to each piece of the distributed information from each user. Therefore, the distributor can know what kind of distributed information can obtain higher evaluation by confirming the number of pieces of evaluation provided to the distributed information.

It is then judged whether or not input operation of providing evaluation to the distributed information which has been listened to is performed (S112). For example, in the case where the reproduction terminal 30B is a wearable terminal, whether or not evaluation is provided to the distributed information may be input through gesture action of the user. Specifically, in the case where the reproduction terminal 30B is an earphone-type terminal, providing evaluation may be input through user action of nodding, and not providing evaluation may be input through action of shaking his/her head. Note that input operation to the reproduction terminal 30B may be performed through the gesture action as described above also in other input. These kinds of input operation to the reproduction terminal 30B can be detected by various kinds of sensors such as, for example, a proximity sensor, an acceleration sensor and a gyro sensor provided at the reproduction terminal 30B.

In the case where input indicating that evaluation is not provided to the distributed information which has been listened to is performed from the user (S112: No), the reproduction terminal 30B finishes the processing of providing evaluation (S110) to the distributed information, and the processing transitions to processing of providing a comment (S120) to the distributed information which has been listened to. Meanwhile, in the case where input indicating that evaluation is provided to the distributed information which has been listened to is performed from the user (S112: Yes), the reproduction terminal 30B transmits information indicating that evaluation is provided to the distributed information to the information processing server 10 (S113).

Note that, in the case where evaluation is provided to the distributed information from the user, the reproduction terminal 30B may reproduce voice information expressing thanks, or the like, to the user from the distributor of the distributed information. Meanwhile, in the case where evaluation is not provided to the distributed information from the user, the reproduction terminal 30B may reproduce voice information expressing disappointment, or the like, to the user from the distributor of the distributed information. Further, content of these kinds of voice information may be changed on the basis of history of provision of evaluation by the user. For example, in the case where the user provides evaluation to a plurality of pieces of distributed information, these kinds of voice information may be changed to content such as "thank you as always". Further, in the case where the user rarely provides evaluation to the distributed information, these kinds of voice information may be changed to content which requests provision of evaluation.

Next, processing of providing a comment to the distributed information which has been listened to is performed (S120). The processing of providing a comment to the distributed information will be described with reference to FIG. 5. Specifically, as illustrated in FIG. 5, first, guide voice which confirms whether or not a comment is provided to the distributed information which has been listened to is reproduced (S121).

The guide voice which confirms whether or not a comment is provided may include description regarding input operation for selecting each of a case where a comment is provided and a case where a comment is not provided in a similar manner to the processing of providing evaluation. Reproduction of these kinds of guide voice may be canceled in the case where input operation is performed from the user.

It is then judged whether or not input operation of providing a comment to the distributed information which has been listened to is performed (S122). For example, as described above, in the case where the reproduction terminal 30B is an earphone-type terminal, providing a comment may be input through the user action of nodding and not providing a comment may be input through action of shaking his/her head in a similar manner to the processing of providing evaluation.

In the case where input of not providing a comment to the distributed information which has been listened to is performed from the user (S122: No), the reproduction terminal 30B finishes the processing of providing a comment (S120) to the distributed information and confirms whether or not there still exists distributed information which has not been listened to (S105). In the case where there still exists distributed information which has not been listened to (S105: Yes), the processing returns to S103, and the reproduction terminal 30B reproduces the distributed information which has not been listened to. Meanwhile, in the case where there is no distributed information which has not been listened to (S105: No), the reproduction terminal 30B finishes reproduction of the distributed information.

In the case where a comment is provided to the distributed information which has been listened to from the user (S122: Yes), the reproduction terminal 30B collects the comment to the distributed information from the user as the voice information (S123).

Subsequently, guide voice which confirms whether or not to listen to the voice information of the collected comment is reproduced (S124), and it is judged whether or not input operation which desires to listen to the voice information of the comment provided by himself/herself to the distributed information is performed (S125). For example, as described above, in the case where the reproduction terminal 30B is an earphone-type terminal, listening to the voice information of the comment may be input through the user action of nodding and not listening to the voice information of the comment may be input through action of shaking his/her head.

In the case where the user desires to listen to the voice information of the comment (S125: Yes), the reproduction terminal 30B reproduces the voice information of the comment provided by the user to the distributed information (S126). Thereafter, the reproduction terminal 30B reproduces guide voice which confirms whether or not the user desires to listen to the voice information of the comment provided by the user, again (S124).

Meanwhile, in the case where the user does not desire to listen to the voice information of the comment (S125: No), guide voice which confirms whether or not to transmit the voice information of the comment provided by the user is reproduced (S127), and, thereafter, it is judged whether or not input operation of transmitting the voice information of the provided comment is performed (S128). For example, as described above, in the case where the reproduction terminal 30B is an earphone-type terminal, transmitting the comment provided to the distributed information may be input through the user action of nodding, and not transmitting the comment provided to the distributed information may be input through action of shaking his/her head.

Note that, in the case where a comment to the distributed information is transmitted, the reproduction terminal 30B may reproduce voice information expressing thanks, or the like, to the user from the distributor of the distributed information. Meanwhile, in the case where a comment to the distributed information is not transmitted, the reproduction terminal 30B may reproduce voice information expressing disappointment, or the like, to the user from the distributor of the distributed information. Further, content of these kinds of voice information may be changed on the basis of history of provision of comments to the distributed information by the user. For example, in the case where the user provides comments to a plurality of pieces of distributed information, these kinds of voice information may be changed to content such as "thank you as always". Meanwhile, in the case where the user rarely provides comments to the distributed information, these kinds of voice information may be changed to content which requests provision of a comment.

In the case where input operation of transmitting a comment to the distributed information is performed (S128: Yes), the voice information of the comment provided to the distributed information by the user is transmitted to the information processing server 10 (S129). Meanwhile, in the case where input operation of not transmitting the comment to the distributed information is performed (S128: No), the processing of providing a comment (S120) to the distributed information is finished, and it is confirmed whether or not there still exists distributed information which has not been listened to (S105). In the case where there still exists distributed information which has not been listened to (S105: Yes), the processing returns to S103, and the reproduction terminal 30B continues reproduction of the distributed information which has not been listened to. Meanwhile, in the case where there is no distributed information which has not been listened to (S105: No), the reproduction terminal 30B finishes reproduction of the distributed information.

According to the operation as described above, in the information processing system according to the present embodiment, in the case where the user wears the reproduction terminal 30B, it is possible to confirm the distributed information from the distributor and cause the user to listen to the distributed information.

Here, there is a possibility that the comment to the distributed information from the user may include content inappropriate to be conveyed to the distributor. Therefore, the information processing server 10 may perform voice recognition processing on each comment from the user and extract a comment including an inappropriate word (hereinafter, also referred to as an error word). The comment extracted as including an error word may be, for example, deleted, or the like, so as not to be conveyed to the distributor.

Figure 6:
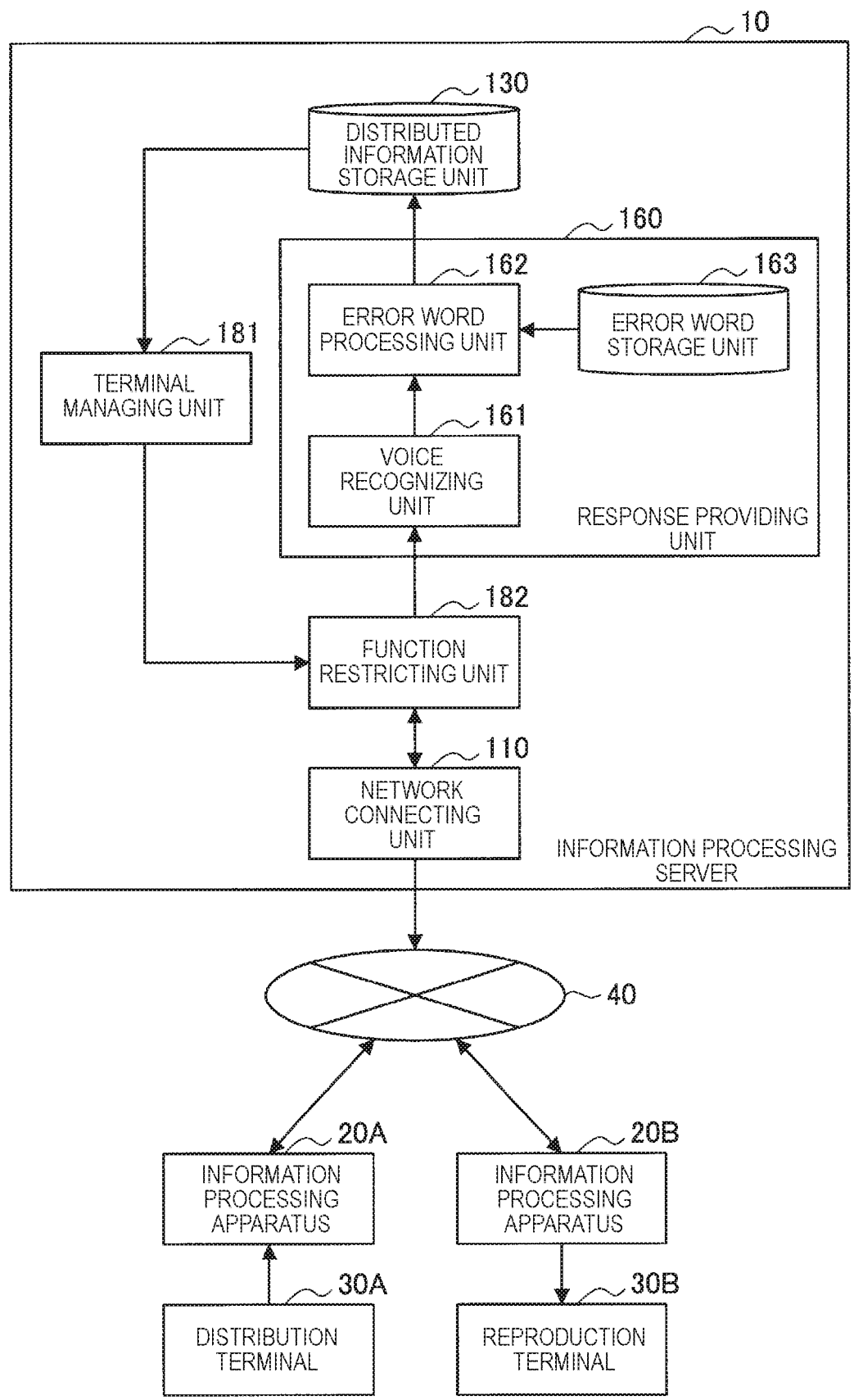
FIG. 6 is a block diagram illustrating extracted components where error word processing is performed on a comment from a user in the information processing server.

A configuration for extracting such an error word will be described with reference to FIG. 6. FIG. 6 is a block diagram illustrating an extracted configuration where error word processing is performed on a comment from the user at the information processing server 10. To simplify illustration, illustration of some components illustrated in FIG. 2A and FIG. 2B is omitted in FIG. 6.

As illustrated in FIG. 6, in the case where error word processing is performed on the comment from the user, the information processing server 10 further includes a terminal managing unit 181 and a function restricting unit 182, and includes a voice recognizing unit 161, an error word processing unit 162 and an error word storage unit 163 in the response providing unit 160.

The voice recognizing unit 161 converts the comment provided to the distributed information from the user from voice information to text information. Specifically, the voice recognizing unit 161 generates text information corresponding to a waveform spectrum of the voice information using an acoustic model in which text data is associated with voice data, and a language model in which information as to arrangement of words is accumulated through statistical processing. Note that, as a voice recognition technology used at the voice recognizing unit 161, a publicly known technology can be utilized, and arbitrary databases can be used as the above-described acoustic model and language model.

The error word processing unit 162 judges whether or not the comment includes predetermined words stored in the error word storage unit 163 on the basis of the text information of the comment converted by the voice recognizing unit 161. Further, the error word processing unit 162 extracts a comment for which it is judged to include the predetermined words. By this means, the error word processing unit 162 can mechanically extract such a comment so that a comment including the predetermined inappropriate words is not conveyed to the distributor.

The predetermined words (that is, error words) are words inappropriate to be conveyed to the distributor, and the predetermined words are stored in the error word storage unit 163. The words stored in the error word storage unit 163 may be, for example, a word against public policy, a word which reviles or abuses others, or the like. Further, in the error word storage unit 163, in addition to these words, words which should be carefully dealt with for the distributor may be individually stored. As the words stored in the error word storage unit 163, for example, words which are typically inappropriate to be used in conversation may be set as error words, or error words may be individually set by the distributor, or the like.

The terminal managing unit 181 manages each of the users who receive the distributed information. Specifically, in the case where a comment including an error word is extracted by the error word processing unit 162, the terminal managing unit 181 acquires identification information of the user who provides the comment and manages the user who provides the comment including an error word separately from other users. By this means, the terminal managing unit 181 can, for example, individually impose a penalty such as function restriction to the user who provides a comment including an error word.

The function restricting unit 182 restricts functions which can be executed by the user managed by the terminal managing unit 181. Specifically, the terminal managing unit 181 restricts functions which can be executed by the user who provides a comment including an error word in the information processing system according to the present embodiment. For example, the function restricting unit 182 may stop transmission of the distributed information to the reproduction terminal 30B of the user who provides a comment including an error word or may restrict addition of a comment to the distributed information.

Note that there can be a possibility that, depending on accuracy of voice recognition executed by the voice recognizing unit 161, a comment not including an error word may be extracted as a comment including an error word, or comments including error words cannot be all extracted.

Therefore, for example, in the case where it is judged by the error word processing unit 162 that a comment includes an error word, voice information of the comment may be caused to be actually listened to by a third party and identification information of the user to be managed at the terminal managing unit 181 only in the case where it is judged also by the third party that the comment includes an error word.

Further, in the case where a complaint from the user who is judged to provide a comment including an error is received, and it is judged that the comment is erroneously extracted as a result of the voice information of the comment being caused to be actually listened to by the third party, the user may be excluded from management by the terminal managing unit 181. Still further, in the case where a comment including an error word is conveyed to the distributor due to an extraction failure, it is also possible to cause the distributor to report the comment including an error word and cause the terminal managing unit 181 to manage the user who provides the comment including an error word.

While configurations where a comment including an error word is extracted for a comment provided to the distributed information have been described above, these configurations can be also applied to the distributed information. That is, after voice recognition is performed also on the distributed information from the distributor, it may be judged by the error word processing unit 162 whether or not the distributed information includes an error word. In such a case, it is possible to prevent the distributed information including an error word from being transmitted to the user.

Figure 7:
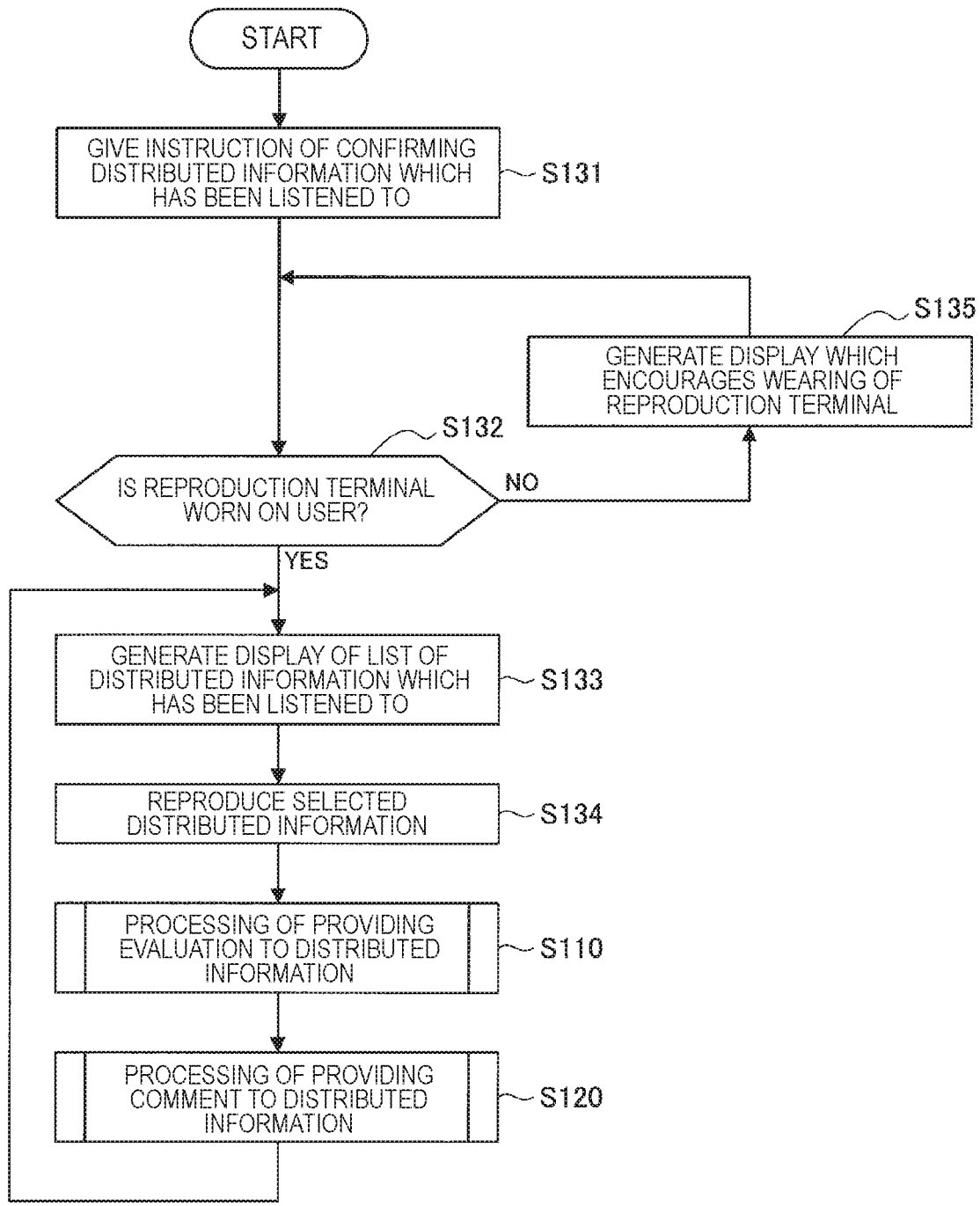
FIG. 7 is a flowchart explaining operation on the reproduction terminal side in the case where distributed which has been listened to once is listened to again.

Further, in the information processing system according to the present embodiment, because the distributed information from the distributor is stored in the distributed information storage unit 130, the user can listen to the distributed information which has been listened to once, again. Operation of the information processing system in such a case will be described with reference to FIG. 7 to FIG. 9. FIG. 7 is a flowchart explaining operation on the reproduction terminal 30B side in the case where the distributed information which has been listened to once is listened to again. Further, FIG. 8 is an explanatory diagram illustrating an example of display which encourages the user to wear the reproduction terminal 30B, and FIG. 9 is an explanatory diagram illustrating an example of display of a list of the distributed information which has been listened to once.

As illustrated in FIG. 7, first, intention that the user desires to confirm the distributed information which has been listened to is input to the information processing apparatus 20B from the user (S131). In this event, the information processing apparatus 20B confirms whether or not the reproduction terminal 30B is worn on the user (S132), and, in the case where the reproduction terminal 30B is not worn on the user (S132: No), display which encourages the user to wear the reproduction terminal 30B is generated (S135).

Figure 8:
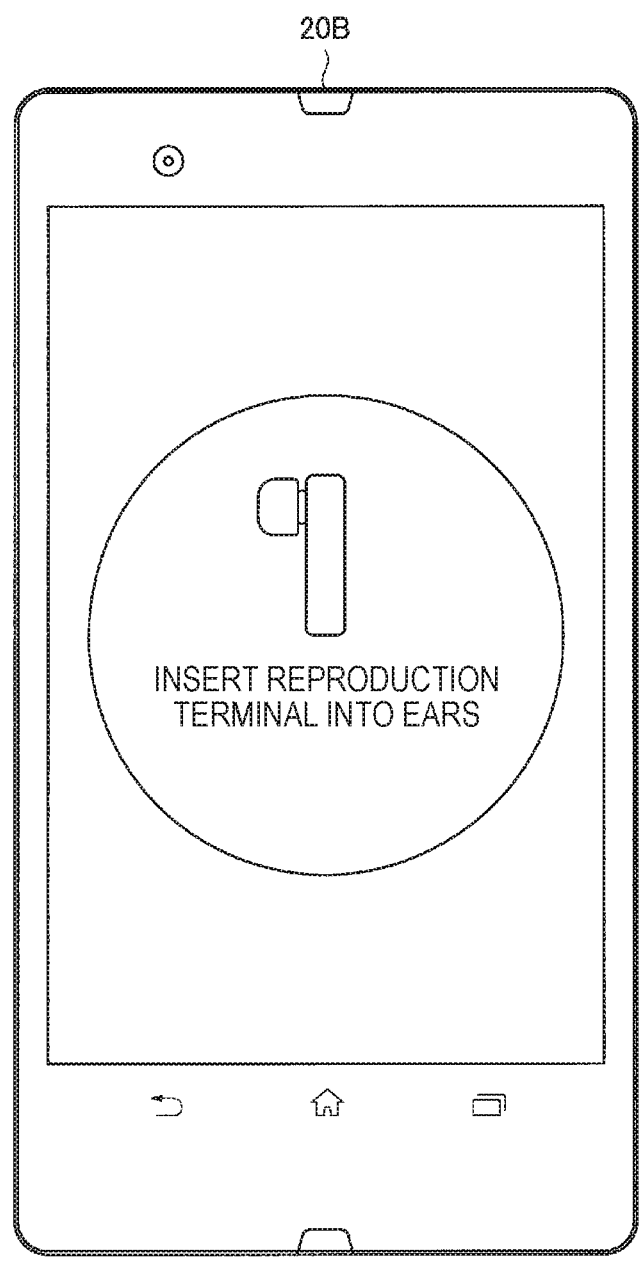
FIG. 8 is an explanatory diagram illustrating an example of display which encourages a user to wear the reproduction terminal.
Figure 9:
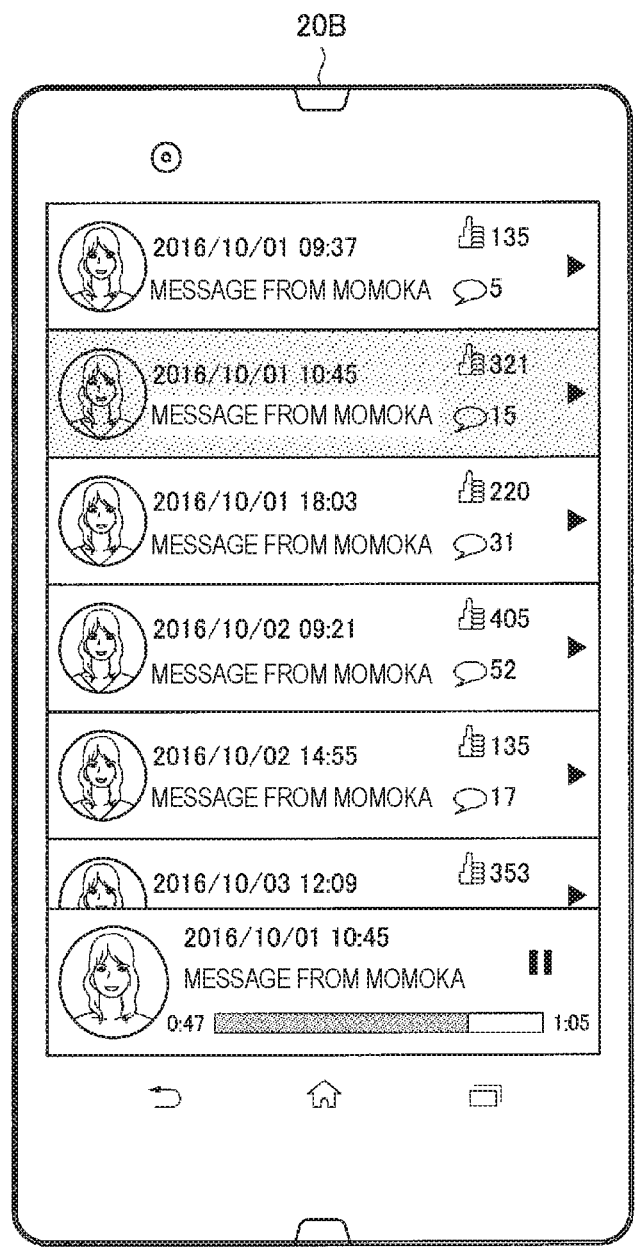
FIG. 9 is an explanatory diagram illustrating an example of display of a list of distributed information which has been listened to once.

The display which encourages the user to wear the reproduction terminal 30B may be, for example, display as illustrated in FIG. 8. Specifically, the display which encourages the user to wear the reproduction terminal 30B may be an image and text indicating a shape of the reproduction terminal 30B and a portion of the body on which the reproduction terminal 30B is to be worn. For example, in the case where the reproduction terminal 30B is an earphone-type terminal, the display which encourages the user to wear the reproduction terminal 30B may be display instructing the user to wear the earphone-type reproduction terminal 30B on the ears.

The information processing apparatus 20B stands by with the display illustrated in FIG. 8 until it is confirmed that the reproduction terminal 30B is worn on the user, and, in the case where the reproduction terminal 30B is worn on the user (S132: Yes), generates display indicating a list of the distributed information which has been listened to (S133).

The display indicating a list of the distributed information which has been listened to may be, for example, display as illustrated in FIG. 9. Specifically, display indicating a list of the distributed information which has been listened to may be display of a list of respective pieces of the distributed information distributed to the reproduction terminal 30B using date and time at which the distributed information is transmitted from the distributors and name and icons, or the like, of the distributors who transmit the distributed information as indexes. Further, as illustrated in FIG. 9, the distributed information which is currently being reproduced may be displayed in an emphasized state by using change of background color, highlighted display, or the like. Still further, display (which is, a so-called seek bar) which indicates the index of the distributed information which is currently being reproduced and a portion of the distributed information which is being reproduced may be provided at a bottom portion of the display of the list. Further, in the display of the list of the distributed information, for each of the distributed information, display such as a check box indicating whether or not evaluation or a comment is provided to the distributed information may be disposed. The user can select distributed information which the user desires to listen to by viewing such display.

In the case where the distributed information to be reproduced is selected from the display of the list of the distributed information, the information processing apparatus 20B causes the reproduction terminal 30B to reproduce the selected distributed information (S134). Here, in the case where evaluation or a comment is not provided to the reproduced distributed information from the user, the processing of providing evaluation (S110) described with reference to FIG. 4 and the processing of providing a comment (S120) described with reference to FIG. 5 may be performed. By this means, the user can provide evaluation or a comment to the reproduced distributed information.

In the case where reproduction of the selected distributed information (S134) is finished, the information processing apparatus 20B displays the list of the distributed information (S133) again. By this means, the user can select the distributed information to be subsequently reproduced. Note that, while operation of the reproduction terminal 30B in the case where the distributed information which has been listened to once is listened to again has been described above with reference to FIG. 7 to FIG. 9, the above-described operation of the reproduction terminal 30B is not limited to such a case. The above-described operation of the reproduction terminal 30B may be applied to a case where distributed information which is listened to for the first time is reproduced.

(Operation on Distribution Terminal Side)

Figure 10:
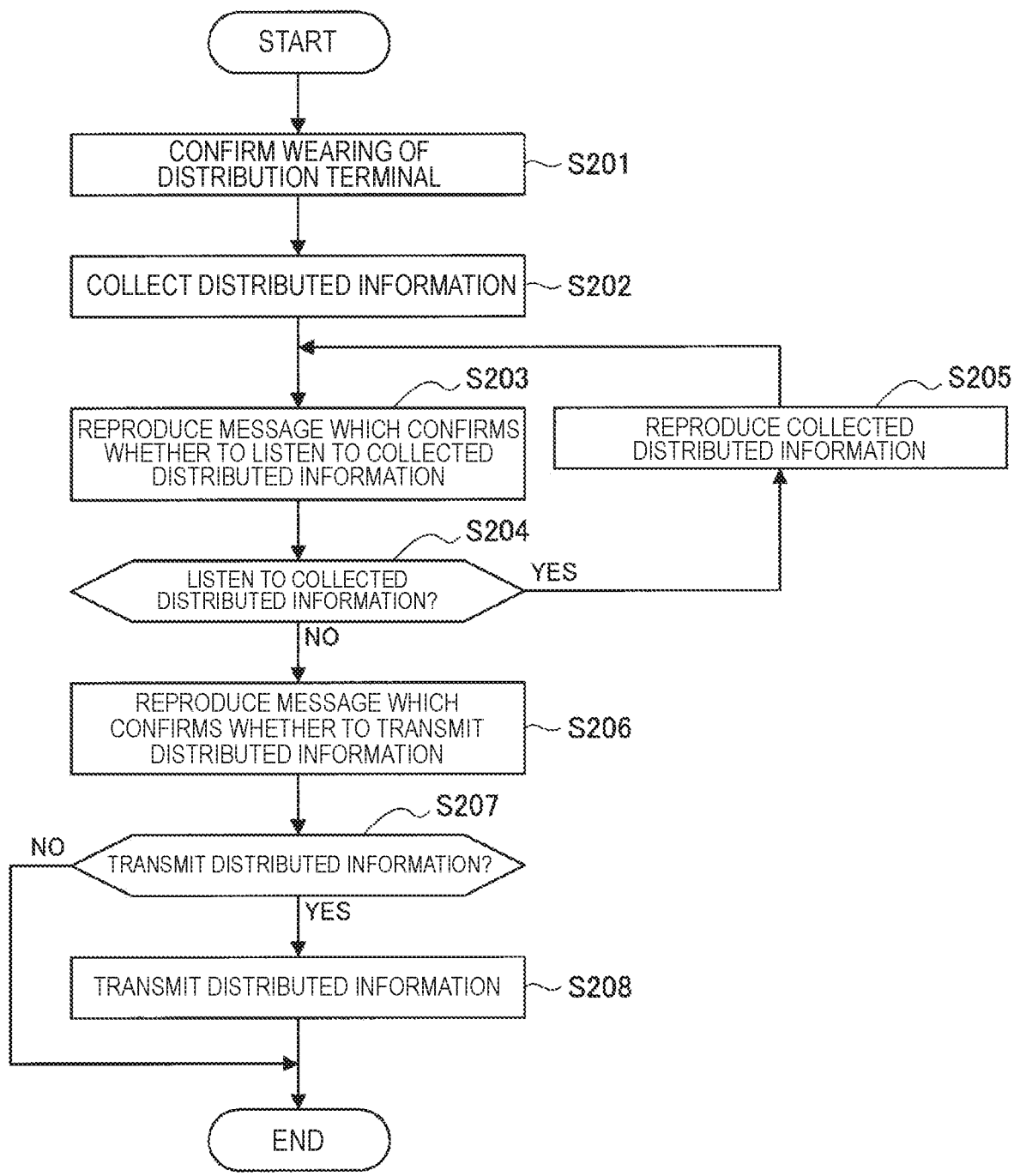
FIG. 10 is a flowchart explaining operation on the distribution terminal side of the information processing system according to the first embodiment.

Subsequently, operation on the distribution terminal 30A side of the information processing system according to the present embodiment will be described with reference to FIG. 10 to FIG. 12. FIG. 10 is a flowchart explaining the operation on the distribution terminal 30A side of the information processing system according to the present embodiment.

As illustrated in FIG. 10, in the information processing system according to the present embodiment, in the case where the distributor transmits the distributed information, first, it is detected that the distribution terminal 30A is worn on the distributor (S201). Then, collection of the distributed information which is voice information from the microphone unit 315 is started in response to operation, or the like, from the distributor (S202). A timing at which collection of the distributed information is finished may be, for example, after a predetermined time period since the collection is started or may be a timing at which the distributor performs operation of finishing the collection on the distribution terminal 30A.

After the collection of the distributed information is finished, guide voice which confirms whether or not to listen to the voice of the collected distributed information is reproduced (S203). Here, the guide voice to be reproduced at the distribution terminal 30A is voice information stored in the distribution terminal 30A, or the like, in advance. While the guide voice to be reproduced at the distribution terminal 30A may be voice uttered by the distributor, the guide voice may be voice uttered by a third party or synthesized voice. Further, as well as the above-described guide voice which confirms whether or not to listen to the voice of the collected distributed information, voice to be reproduced to indicate a state of the distribution terminal 30A or guide the user in the operation, or the like, (which is, so-called, guide voice) may be also voice uttered by the distributor, voice uttered by a third party or synthesized voice in a similar manner.

Thereafter, it is judged whether or not input operation for the distributor to listen to the voice information of the distributed information is performed (S204). For example, in the case where the distribution terminal 30A is an earphone-type terminal, listening to the voice information of the distributed information may be input through the user action of nodding, and not listening to the voice information of the distributed information may be input through action of shaking his/her head.

In the case where input operation of listening to the voice information of the distributed information is performed (S204: Yes), voice of the collected distributed information is reproduced (S205). Thereafter, guide voice which confirms to the distributor whether or not the distributor desires to listen to the voice information of the collected distributed information again is reproduced (S203).

Meanwhile, in the case where input operation of not listening to the distributed information is performed (S204: No), guide voice which confirms whether or not to transmit the collected distributed information is reproduced (S206). Thereafter, it is judged whether or not input operation of desiring transmission of the distributed information is performed from the distributor (S207). For example, as described above, in the case where the reproduction terminal 30B is an earphone-type terminal, transmitting the distributed information may be input through the user action of nodding, and not transmitting the distributed information may be input through action of shaking his/her head.

In the case where input operation of transmitting the distributed information is performed (S207: Yes), after the distributed information uttered by the distributor is transmitted to the information processing server 10 (S208), the distribution terminal 30A finishes the operation. In the case where input operation of not transmitting the distributed information is performed, the distributed information is not transmitted to the information processing server 10 (S207: No), and the distribution terminal 30A finishes the operation.

Note that the distributor is associated with the distribution terminal 30A in advance. By this means, the information processing server 10 can judge a distributor who transmits the received distributed information.

Further, the voice of the distributor may be collected using other apparatuses instead of using the distribution terminal 30A. For example, in the case where the information processing apparatus 20A includes a microphone unit, the information processing apparatus 20A can collect the voice of the distributor and generate the distributed information.

With the operation as described above, in the information processing system according to the present embodiment, it is possible to collect the voice uttered by the distributor to generate the distributed information.

Further, in the information processing system according to the present embodiment, because a response such as a comment from the user is stored in the distributed information storage unit 130 in association with the distributed information, the distributor can also confirm the response to the distributed information from the user. Operation of the information processing system in such a case will be described with reference to FIG. 11. FIG. 11 is a flowchart explaining operation on the distribution terminal 30A side in the case where a comment to the distributed information from the user is confirmed.

Figure 11:
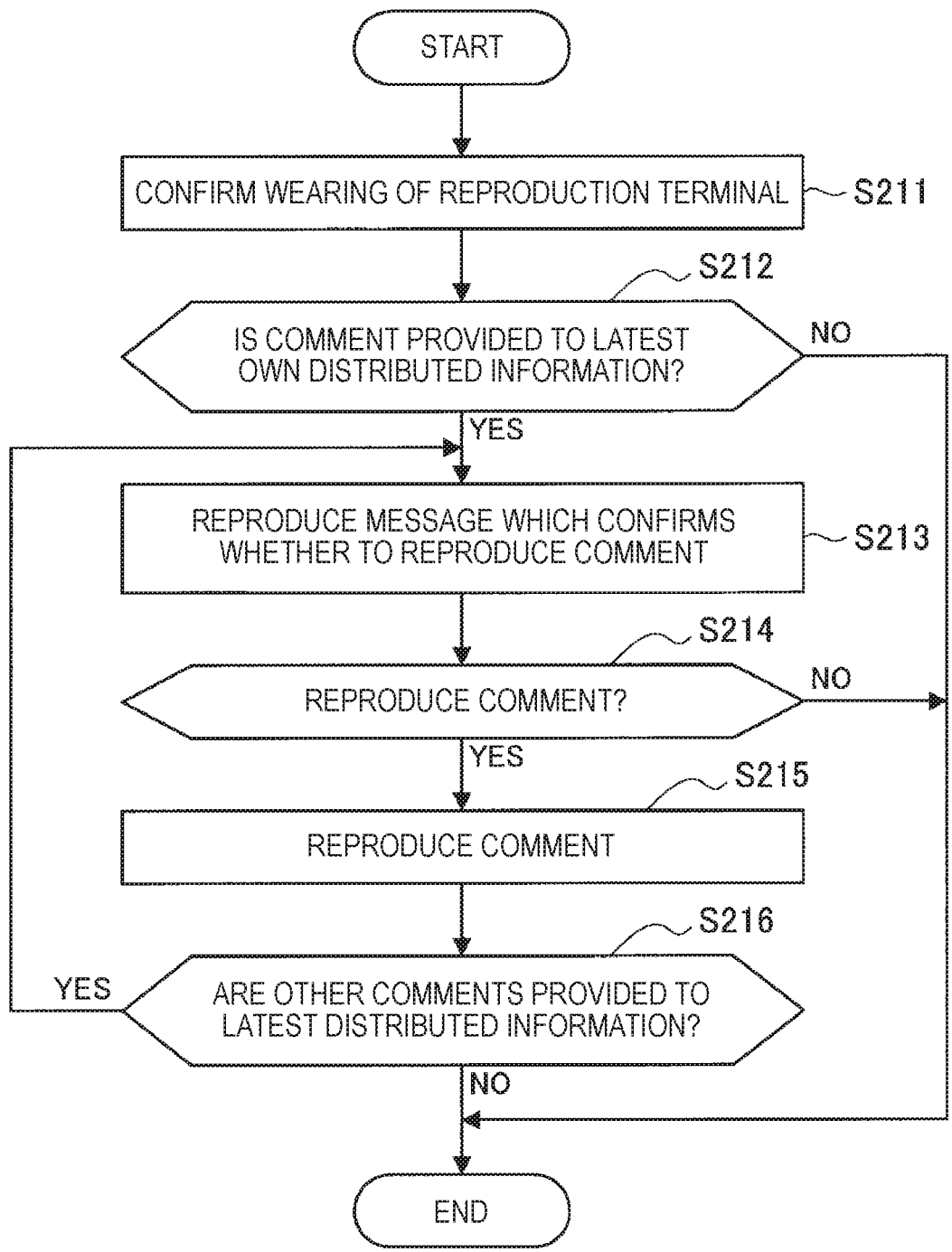
FIG. 11 is a flowchart explaining operation on the distribution terminal side in the case where a comment to the distributed information from the user is confirmed.

As illustrated in FIG. 11, for example, it is detected that the distribution terminal 30A is worn on the distributor (S211). Then, it is confirmed whether or not a comment from the user is provided to the latest distributed information transmitted from the distributor who wears the distribution terminal 30A (S212). In the case where a comment from the user is not provided to the latest distributed information (S212: No), the distribution terminal 30A finishes the operation and puts into a standby state. Note that whether or not a comment from the user is provided to the distributed information can be confirmed by the control unit 312 of the distribution terminal 30A or the control unit 213 of the information processing apparatus 20A making an inquiry as to whether or not there is a comment to the distributed information to the response conveying unit 170 of the information processing server 10 via the network 40.

Meanwhile, in the case where a comment from the user is provided to the latest distributed information (S212: Yes), guide voice which confirms whether or not to reproduce the comment provided to the distributed information is reproduced (S213). Thereafter, it is confirmed whether or not input operation indicating that the distributor desires reproduction of the comment is performed (S214). For example, as described above, in the case where the distribution terminal 30A is an earphone-type terminal, reproducing the comment may be input through the user action of nodding, and not reproducing the comment may be input through action of shaking his/her head.

In the case where input operation indicating that the distributor does not desire reproduction of the comment is performed (S214: No), the distribution terminal 30A finishes the operation and puts into a standby state. Meanwhile, in the case where input operation indicating that the distributor desires reproduction of the comment is performed (S214: Yes), the distribution terminal 30A reproduces voice information including the comment from the user provided to the latest distributed information (S215).

Thereafter, it is confirmed whether or not a plurality of comments is provided to the distributed information (S216). In the case where a plurality of comments is not provided to the distributed information (S216: No), the distribution terminal 30A finishes the operation and puts into a standby state. Meanwhile, in the case where a plurality of comments is provided to the distributed information, the processing returns to S213, and guide voice which confirms whether or not to reproduce the next comment is reproduced, and, as described above, voice information including the comment provided to the distributed information is reproduced. The distribution terminal 30A repeats the above-described operation of reproducing a comment until reproduction of all the comments provided to the distributed information is finished.

Note that reproduction of the plurality of comments provided to the distributed information may be performed in chronological order of date and time at which the comment is provided or may be performed in reverse chronological order of date and time at which the comment is provided.

Further, the information processing apparatus 20A can cause the distributor to perform confirmation through display of the comment and the evaluation provided to the distributed information from the user. The display presented at the information processing apparatus 20A in such a case will be described with reference to FIG. 12. FIG. 12 is an explanatory diagram illustrating an example of display in which the distributed information is associated with the comments to the distributed information.

For example, in the display illustrated in FIG. 12, a list of the respective pieces of the distributed information transmitted from the distribution terminal 30A is illustrated using date and time of transmission, name and icons of the distributors who has transmitted the distributed information, or the like, as indexes. Further, an image indicating the number of pieces of the provided evaluation, and the number of provided comments is associated with each piece of the distributed information. For example, the image indicating the provided evaluation may be an image of thumb-up, and the image indicating the provided comment may be an image of a voice balloon. The number of pieces of the provided evaluation and comments may be, for example, displayed with the number, or the like, next to these images.

Note that, in the case where there is a plurality of distributors, the respective distributors may be able to confirm only the own distributed information and comments provided to the own distributed information, or may be able to further confirm the distributed information of other distributors, or may be able to further confirm the distributed information of other distributors and comments provided to the distributed information.

Further, in the case where each piece of the distributed information is selected, display transitions to display indicating details of the selected distributed information. In the display indicating details of the distributed information, a list of comments provided to the distributed information is indicated. For example, a list of the respective provided comments may be displayed using date and time at which the comments are provided, and identification information and icons of the users who have provided the comments as indexes. The distributor can listen to the voice information of the selected comment by selecting each of the displayed comments.

Note that, in the case where the voice information of the comment is converted into text information by being subjected to the voice recognition technology, in the display indicating details of the distributed information, the converted text information may be used as an index of each comment.

[1.4. Modified Examples]

While the information processing system according to the present embodiment has been described above, there can be various other modified examples for the information processing system according to the present embodiment as described below.

(Coordination with Other Application)

The information processing system according to the present embodiment can perform operation in coordination with an external information processing server or an external application program (such as, for example, social networking service).

For example, the distributed information may be converted into text information by the voice recognition technology being applied to the distributed information which is voice information, and the converted text information may be distributed to external social networking service (SNS), or the like, at the same time as distribution of the distributed information in the information processing system according to the present embodiment. Further, announcement indicating that the distributed information is transmitted may be made at the external SNS, or the like, at the same time as transmission of the distributed information in the information processing system according to the present embodiment. Further, a text message of the distributor which has been posted at the external SNS, or the like, may be converted into voice for reading and may be transmitted as the distributed information in the information processing system according to the present embodiment. Note that examples of the external SNS can include, for example, short sentence posting service.

(Coordination with Location Information)

Further, the information processing system according to the present embodiment can perform operation in coordination with location information acquired by the information processing apparatus 20B or the reproduction terminal 30B.

Note that the location information can be acquired by using, for example, a global navigation satellite system (GNSS) sensor, or the like. Further, the location information can be calculated using signal strength from each base station in a mobile communication network, or can be calculated using signal strength from each access point of Wi-Fi (registered trademark).

According to this, for example, it is possible to control the information processing system so that predetermined distributed information is reproduced in the case where the information processing apparatus 20B or the reproduction terminal 30B enters a predetermined location.

For example, in the case where the distributor is an idol, or the like, the predetermined location may be the latest or the past concert venue, the latest or the past event site, a location related to the distributor (such as, for example, hometown or a memorable location), or the like. The distributed information reproduced in this event may be, for example, explanation of the predetermined location by the distributor, guide of the surrounding place or explanation of memory, or the like.

Further, it is also possible to control the information processing system so that predetermined distributed information is reproduced in the case where the information processing apparatus 20B or the reproduction terminal 30B passes through a plurality of predetermined locations. For example, in the case where the information processing apparatus 20B or the reproduction terminal 30B passes through a plurality of predetermined locations, the predetermined distributed information may be reproduced at the reproduction terminal 30B as privilege or reward.

Further, the information processing system can perform operation in coordination with a behavior log, or the like, of the user, which has been acquired by the information processing apparatus 20B or the reproduction terminal 30B in addition to the location information. In such a case, for example, it is possible to control the information processing system so that the predetermined distributed information is reproduced in the case where the user takes predetermined behavior at the predetermined location.

Figure 13:
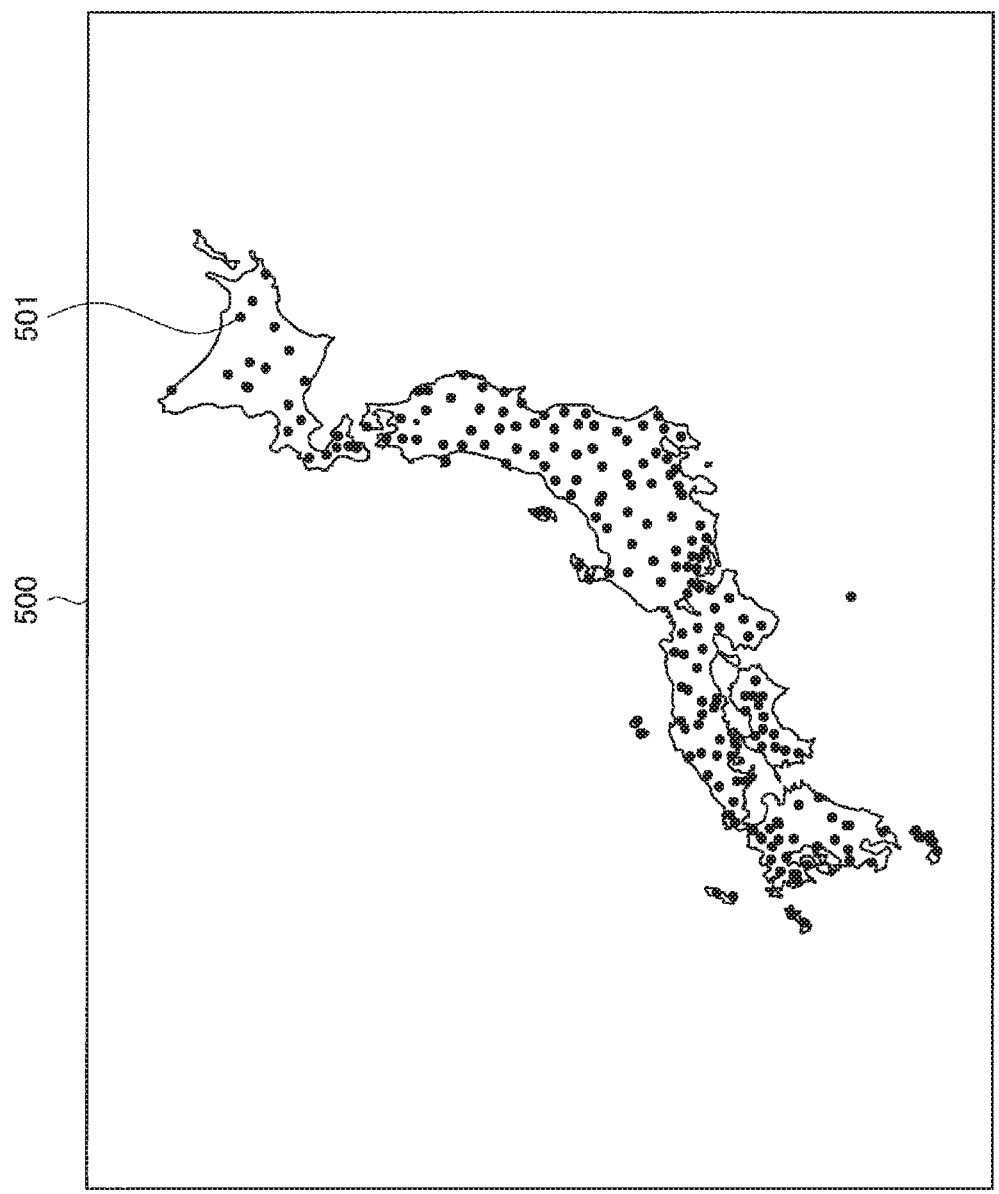
FIG. 13 is an explanatory diagram illustrating an example of display in which responses such as comments and evaluation are associated with location information of the user.

Further, the information processing system according to the present embodiment can indicate a response such as a comment or evaluation from the user to the distributor in accordance with the location information of the user. For example, as illustrated in FIG. 13, the information processing system according to the present embodiment can indicate display in which locations of the users who provide the comments or the evaluation to the distributed information are disposed with dots 501, or the like, on a map 500. According to this, the information processing system can further increase a sense of intimacy between the distributor and the users by specific locations of the users who have provided the comments or the evaluation being indicated.

(Usage as Filtering Function)

Further, the information processing system according to the present embodiment enables distribution of the distributed information between the distributor and the user who are located at the same location such as a concert venue, as well as distribution of the distributed information between the distributor and the user who are located at remote locations.

For example, in the case where there is a plurality of distributors, who are idols, or the like, it is also possible to cause only voice of a specific distributor to be reproduced at the reproduction terminal 30B as the distributed information at the concert venue of the distributors. That is, in such a case, the information processing system according to the present embodiment can execute a filtering function of extracting voice of the specific distributor among the plurality of distributors and transmitting the voice to the user as the distributed information.

(Modified Examples of Distributed Information)

While, in the above description, the distributed information to be distributed in the information processing system according to the present embodiment is information such as voice information, which depends on physicality of the distributor, the technology according to the present disclosure is not limited to the above-described examples. For example, the distributed information distributed in the information processing system according to the present embodiment may be content information including various kinds of content such as music, an image, a moving image and text.

2. Second Embodiment

[2.1. Outline of Information Processing System]

Figure 14:
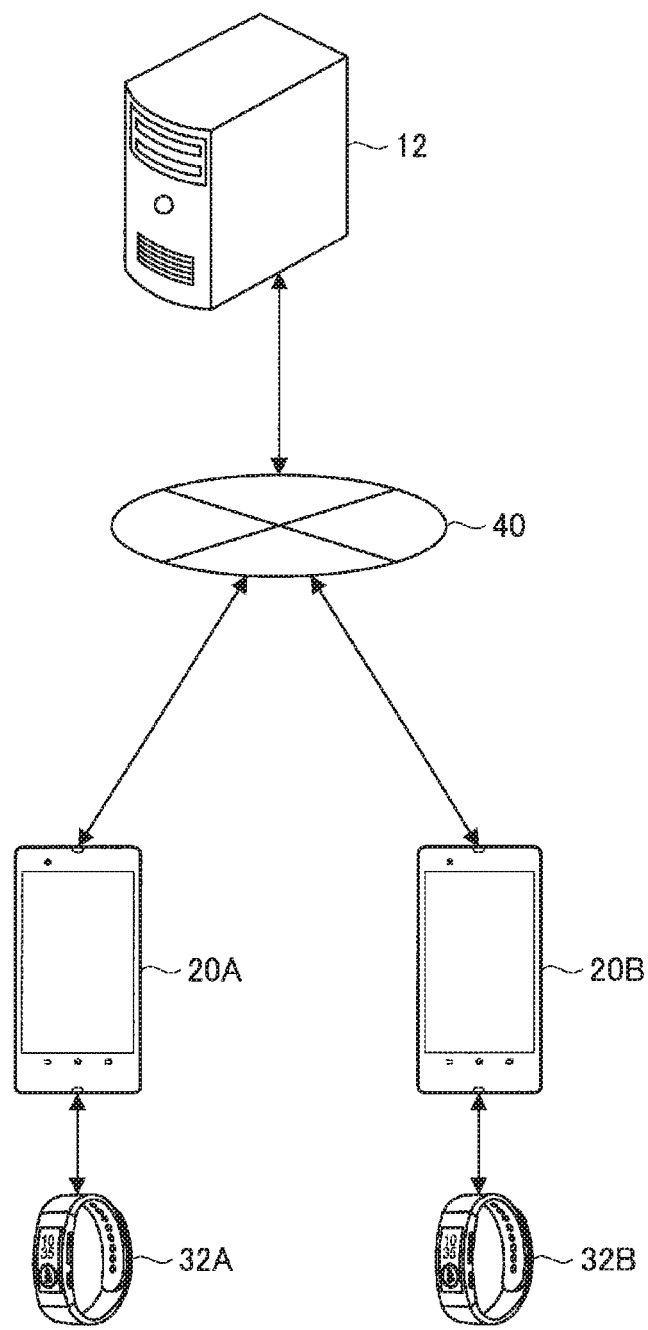
FIG. 14 is an explanatory diagram explaining outline of an information processing system according to a second embodiment of the present disclosure.

Next, outline of an information processing system according to a second embodiment of the present disclosure will be described with reference to FIG. 14. FIG. 14 is an explanatory diagram explaining the outline of the information processing system according to the second embodiment of the present disclosure.

As in the first embodiment, the information processing system according to the present embodiment is an information distribution system which receives distributed information from a distributer and transmits the distributed information to a user. Note that the distributor is, for example, an idol, celebrity, an opinion leader, or the like, and the user is, for example, a fan, a follower, or the like, of the distributor.

In the present embodiment, the distributed information may be, for example, distributed information depending on physicality of the distributor, or may be vibration information which conveys a tactile sense or heartbeat of the distributor. Because the tactile sense of the distributor is information depending on an object which the distributor actually touches, and the heartbeat of the distributor is information depending on feeling, or the like, of the distributor, both are information having strong concreteness. Therefore, in the information processing system according to the present embodiment, it is possible to induce a sense as if the user shares space with the distributor by distributing these kinds of information as the distributed information.

As illustrated in FIG. 14, the information processing system according to the present embodiment includes a distribution terminal 32A and an information processing apparatus 20A possessed by the distributor, a reproduction terminal 32B and an information processing apparatus 20B possessed by the user who receives the distributed information, and an information processing server 12 connected to the information processing apparatuses 20A and 20B via a network 40.

Note that, because the information processing apparatus 20A, the information processing apparatus 20B and the network 40 have configurations substantially similar to those described in the first embodiment, description will be omitted here.

The distribution terminal 32A and the reproduction terminal 32B are, for example, information processing apparatuses worn on any portion of the body of the distributor or the user. The distribution terminal 32A has at least a heart rate measuring function or a tactile sense detecting function, and the reproduction terminal 32B has at least a vibration reproducing function.

Figure 15A:
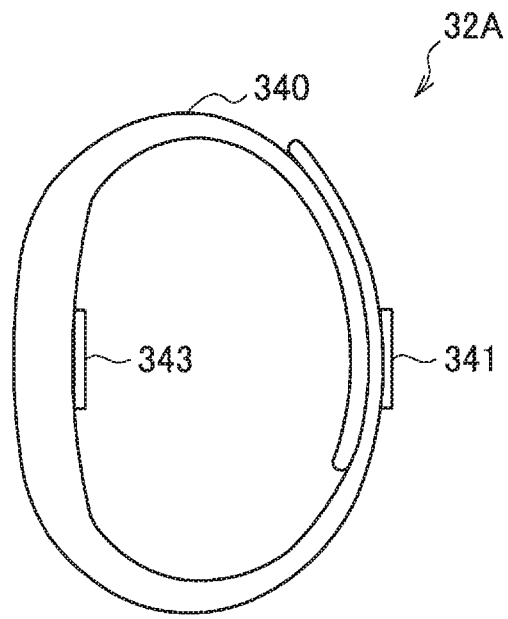
FIG. 15A is a schematic diagram illustrating a specific example of a configuration of a distribution terminal according to the second embodiment.
Figure 15B:
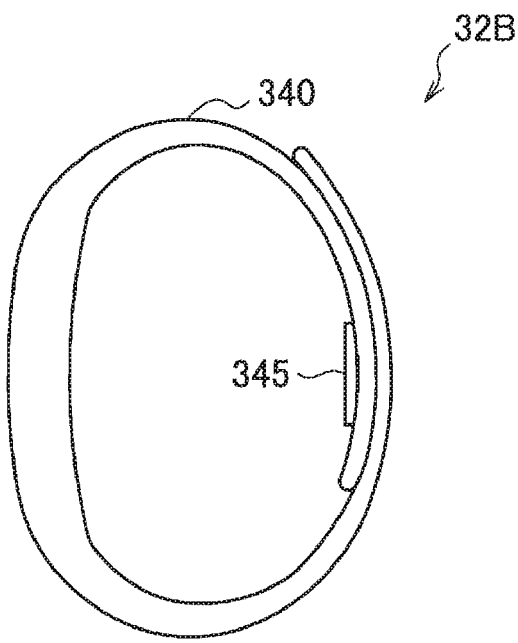
FIG. 15B is a schematic diagram illustrating a specific example of a configuration of a reproduction terminal according to the second embodiment.

Here, the distribution terminal 32A and the reproduction terminal 32B will be described here more specifically with reference to FIG. 15A and FIG. 15B. FIG. 15A is a schematic diagram illustrating a specific example of a configuration of the distribution terminal 32A, and FIG. 15B is a schematic diagram illustrating a specific example of a configuration of the reproduction terminal 32B.

As illustrated in FIG. 15A, the distribution terminal 32A is a wristwatch-type terminal worn on the wrist, or the like, of the distributor, and includes a band portion 340, a pulse sensor 343 and a tactile sensor 341.

The distribution terminal 32A is fixed at the body of the distributor by the band portion 340 being wound around the wrist, or the like, of the distributor. The band portion 340 may be constituted with any material if the band portion 340 can be wound around the wrist, or the like, of the distributor, and may be constituted with any of leather, cloth, a resin, a metal or combination thereof.

The tactile sensor 341 is a sensor which detects a tactile sense of the distributor, and is provided at the band portion 340 on a face opposite to a face facing the wrist, or the like, of the distributor (that is, an external side of the band portion 340). For example, the tactile sensor 341 may include a microphone, or the like. The tactile sensor 341 which includes a microphone, or the like, can acquire a tactile sense of the distributor touching an object, or the like, as air vibration.

The pulse sensor 343 is a sensor which measure a heart rate of the distributor, and is provided at the band portion 340 on a face facing the wrist, or the like, of the distributor (that is, an internal side of the band portion 340). For example, the pulse sensor 343 may measure a heart rate by radiating infrared light to the wrist, or the like, of the distributor and measuring change of blood flow as change of infrared absorption characteristics, or may measure a heart rate by detecting pulsation of a blood vessel by a pressure sensor, or the like.

As illustrated in FIG. 15B, the reproduction terminal 32B is a wristwatch-type terminal worn on the wrist, or the like, of the user, and includes a band portion 340 and a vibration reproducing unit 345.

As in the distribution terminal 32A, the reproduction terminal 32B is fixed at the body of the user by the band portion 340 being wound around the wrist, or the like, of the user. The band portion 340 may be constituted with any material if the band portion 340 can be wound around the wrist, or the like, of the user, and may be constituted with any of leather, cloth, a resin, a metal or combination thereof.

The vibration reproducing unit 345 is an actuator which reproduces the distributed information as vibration, and is provided on a face of the band portion 340, facing the wrist, or the like, of the user (that is, an internal side of the band portion 340). The vibration reproducing unit 345 may include, for example, an eccentric motor, a voice coil motor, a piezo actuator, or the like.

In the information processing system according to the present embodiment, the vibration information which conveys a tactile sense or heartbeat of the distributor is acquired by the distribution terminal 32A as the distributed information is and distributed to the reproduction terminal 32B via the network 40. By the distributed information being reproduced at the reproduction terminal 32B, the user can feel the tactile sense of an object touched by the distributor or the heartbeat of the distributor in a pseudo manner.

Note that the forms of the distribution terminal 32A and the reproduction terminal 32B are not limited to the above-described wristwatch-type, and may be any form. For example, the forms of the distribution terminal 32A and the reproduction terminal 32B may be a spectacle type, a ring type, a headset type, an earphone type, or the like. However, in order that the vibration information is efficiently acquired from the distributor and the acquired vibration information is efficiently conveyed to the user, the forms of the distribution terminal 32A and the reproduction terminal 32B may be the above-described wristwatch type.

The distribution terminal 32A and the reproduction terminal 32B transmit/receive the distributed information to/from the information processing server 12 via the information processing apparatuses 20A and 20B. However, the distribution terminal 32A and the reproduction terminal 32B may directly transmit/receive the distributed information to/from the information processing server 12 without intervening the information processing apparatuses 20A and 20B.

The information processing server 12 receives the distributed information from the distribution terminal 32A and controls transmission of the distributed information to the reproduction terminal 32B on the basis of whether the user wears the reproduction terminal 32B.

Specifically, in the case where the user wears the reproduction terminal 32B upon receipt of the distributed information, the information processing server 12 transmits the distributed information to the reproduction terminal 32B. Meanwhile, in the case where the user does not wear the reproduction terminal 32B upon receipt of the distributed information, the information processing server 12 does not transmit the distributed information to the reproduction terminal 32B. However, in the case where whether or not the user can receive the distributed information is controlled at the reproduction terminal 32B, the information processing server 12 may control transmission of the distributed information to the reproduction terminal 32B on the basis of whether or not the user can receive the distributed information. According to this, in the case where the user always wears the reproduction terminal 32B, the user can control whether or not the user can receive the distributed information at the reproduction terminal 32B.

The distributed information in the present embodiment is vibration information which conveys a tactile sense or heartbeat of the distributor. The information processing server 12 can cause the distributed information to be directly conveyed to the body of the user by controlling transmission of the distributed information so that the distributed information is reproduced in a state where the user wears the reproduction terminal 32B. By this means, the information processing server 12 enables the user to experience a sense or feeling of the distributor in a pseudo manner.

Therefore, according to the information processing system according to the present embodiment, it is possible to distribute vibration information which conveys a tactile sense or heartbeat depending on physicality of the distributor to the user more effectively.

Note that, while, in FIG. 14, an example has been described where the information processing system includes the distribution terminal 32A, the information processing apparatus 20A, the information processing server 12, the information processing apparatus 20B and the reproduction terminal 30B, the technology according to the present disclosure is not limited to such an example. For example, the distribution terminal 32A and the information processing apparatus 20A may be one integrated information processing apparatus, and the reproduction terminal 32B and the information processing apparatus 20B may be one integrated information processing apparatus. Further, part or all of the functions of the information processing server 12 may be executed at one of the information processing apparatus 20A and the information processing apparatus 20B.

[2.2. Configuration of Information Processing System]

A configuration of the information processing system according to the present embodiment will be described next with reference to FIG. 16. FIG. 16 is a block diagram explaining a specific configuration of the information processing system according to the present embodiment.

As illustrated in FIG. 16, the distribution terminal 32A includes a distributed information acquiring unit 314, a control unit 312 and a communication unit 311, and the information processing server 12 includes a network connecting unit 110, a distributed information receiving unit 120, a distribution control unit 140 and a distributed information transmitting unit 150, and the reproduction terminal 32B includes a sensor unit 325, a reproduction control unit 326, a communication unit 321 and a reproducing unit 327.

Note that, because the information processing apparatus 20A, the information processing apparatus 20B, the network 40, the communication unit 311, the network connecting unit 110 and the communication unit 321 have configurations substantially similar to those described in the first embodiment, description will be omitted here.

(Distribution Terminal 32A)

The distributed information acquiring unit 314 includes, for example, a tactile sensor 341 or a pulse sensor 343, and acquires information regarding a tactile sense or a heart rate of the distributor who wears the distribution terminal 32A. Specifically, the distributed information acquiring unit 314 may acquire the tactile sense of the distributor at the tactile sensor 341 as vibration and may generate vibration information which conveys the tactile sense of the distributor. Further, the distributed information acquiring unit 314 may acquire a heart rate of the distributor at the pulse sensor 343 and may generate vibration information which conveys the heartbeat of the distributor. For example, the vibration information is information regarding vibration in the case where the distributor touches an object, information regarding the heart rate of the distributor, or the like.

For example, in the case where the information regarding the heart rate of the distributor is distributed as the distributed information, the distribution terminal 32A may distribute a timing at which a heart of the distributor beats as the distributed information in addition to the heart rate of the distributor. In such a case, because the reproduction terminal 32B can reproduce vibration in synchronization with the timing at which the heart of the distributor beats, it is possible to cause the user to experience feeling, or the like, of the distributor in a pseudo manner more specifically. In such a case, the distribution terminal 32A may transmit the distributed information with a predetermined period such as every five seconds.

The control unit 312 includes, for example, an MPU which is an arithmetic processing unit, and a memory in which a control program, a control parameter, or the like, are stored, and controls each component of the distribution terminal 32A. Specifically, the control unit 312 controls each component so that the vibration information acquired by the distributed information acquiring unit 314 is transmitted to the information processing apparatus 20A as the distributed information.

(Information Processing Server 12)

The distributed information receiving unit 120 receives the distributed information transmitted from the distribution terminal 32A via the information processing apparatus 20A. The distributed information is information depending on physicality of the distributor, and is vibration information generated at the distributed information acquiring unit 314 of the distribution terminal 32A. The information processing server 12 can cause the user to have an experience of the distributor or experience feeling of the distributor in a pseudo manner by conveying the distributed information transmitted from the distributor to the user.

The distribution control unit 140 controls transmission of the distributed information to the reproduction terminal 32B on the basis of whether the user wears the reproduction terminal 32B. Specifically, in the case where the user wears the reproduction terminal 32B, the distribution control unit 140 controls a timing for transmitting the distributed information so that the distributed information is reproduced at the reproduction terminal 32B. Therefore, in the case where the user does not wear the reproduction terminal 32B, the distribution control unit 140 does not transmit the distributed information to the reproduction terminal 32B. By this means, the distribution control unit 140 can cause the distributed information to be directly conveyed to the user through the reproduction terminal 32B. Further, in the case where the user does not wear the reproduction terminal 32B, it is possible to prevent power from being consumed due to vibration, or the like, of the reproduction terminal 32B.

The distributed information transmitting unit 150 transmits the distributed information to the reproduction terminal 32B on the basis of control by the distribution control unit 140. Specifically, in the case where the user wears the reproduction terminal 32B, the distributed information transmitting unit 150 instantaneously transmits the distributed information received at the distributed information receiving unit 120 to the reproduction terminal 32B. By this means, because the distributed information transmitting unit 150 can cause the user to feel the tactile sense or the heartbeat of the distributor in real time as the distributed information, it is possible to strengthen special feeling that the distributor and the user share experience or space. Further, the distributed information transmitting unit 150 does not transmit the distributed information distributed from the distributor in the case where the user does not wear the reproduction terminal 32B to the reproduction terminal 32B.

(Reproduction Terminal 32B)

The sensor unit 325 is various kinds of sensors mounted on the reproduction terminal 32B. The sensor unit 325 includes at least a sensor which acquires information to be used in the case where it is judged whether or not the reproduction terminal 32B is worn on the user. For example, the sensor unit 325 may include a proximity sensor which judges whether or not the reproduction terminal 32B is worn on the user, a touch sensor which detects touch between the reproduction terminal 32B and an object, or the like, and may judge whether or not the reproduction terminal 32B is worn on the user on the basis of information acquired by these sensors.

Further, the sensor unit 325 may include a microphone which collects voice of the user, and may include an acceleration sensor, a gyro sensor or a vibration sensor which detects gesture of the user. In the case where the sensor unit 325 includes such a sensor, the user can intuitively perform input to the reproduction terminal 32B without intervening an input device such as a touch panel, a keyboard, a button, a microphone, a switch and a lever.

The reproducing unit 327 includes, for example, an actuator which generates vibration and a signal processing circuit, and reproduces the distributed information. Specifically, the reproducing unit 327 reproduces the distributed information transmitted from the information processing server 12 as vibration.

Note that the reproducing unit 327 may include a light source such as a light emitting diode (LED). The reproducing unit 327 may cause the light source to blink in synchronization with the vibration. According to this, the reproducing unit 327 can explicitly indicate the vibration to the user.

The reproduction control unit 326 includes, for example, an MPU which is an arithmetic processing apparatus, and a memory in which a control program, a control parameter, or the like, are stored, and controls reproduction of the distributed information received from the information processing apparatus 20B. Specifically, the reproduction control unit 326 may cause the vibration which conveys the tactile sense of the distributor to be reproduced at the reproducing unit 327 on the basis of the information regarding the vibration in the case where the distributor touches an object. Further, the reproduction control unit 326 may cause the reproducing unit 327 to reproduce the vibration in synchronization with the heartbeat of the distributor on the basis of the information regarding the heart rate of the distributor. Note that the reproduction control unit 326 may be provided at the information processing apparatus 20B, and may control vibration of the reproducing unit 327 through communication, or the like.

For example, in the case where the reproduction control unit 326 causes the reproducing unit 327 to reproduce the vibration in synchronization with the heartbeat of the distributor on the basis of the information regarding the heart rate of the distributor, the reproduction control unit 326 may cause the reproducing unit 327 to reproduce vibration closer to the heartbeat. In such a case, the reproduction control unit 326 can convey the heartbeat of the distributor to the user with vibration which provides a less feeling of strangeness and which seems real.

Figure 17:
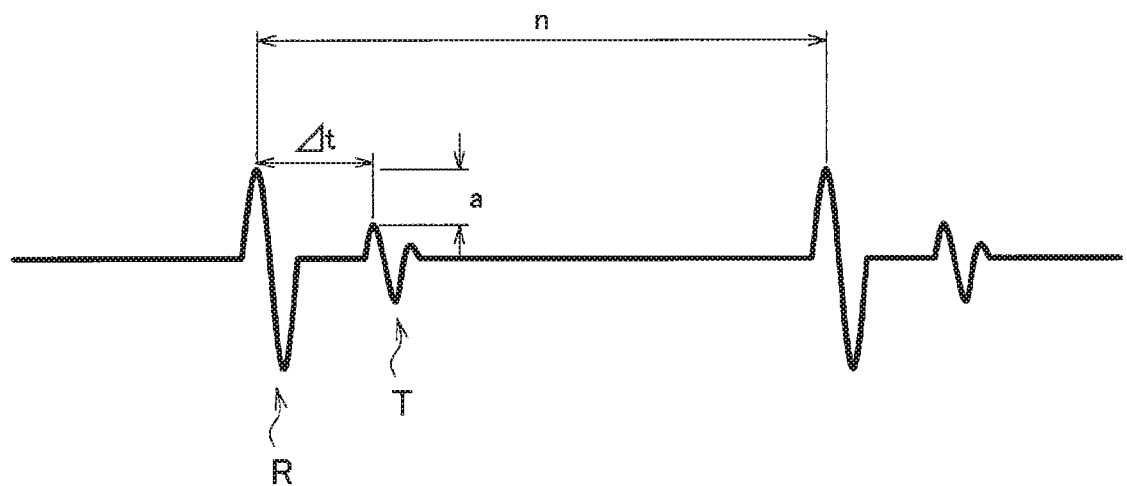
FIG. 17 is a graph schematically illustrating a waveform of heartbeat.

Here, an aspect of the heartbeat will be described more specifically with reference to FIG. 17 and FIG. 18. FIG. 17 is a graph schematically illustrating a waveform of the heartbeat, and FIG. 18 is a graph schematically illustrating relationship between Δt and a illustrated in FIG. 17 and the heart rate.

As illustrated in FIG. 17, the heart contracts and thereafter dilates in one-time heartbeat. Therefore, a waveform of one-time heartbeat is mainly constituted with two waveforms. Specifically, a waveform of one-time heartbeat is constituted with a waveform R which has a sharp peak and corresponds to contraction of the heart, and a waveform T which has a wide peak and corresponds to dilation of the heart. Note that an interval n of the waveform R corresponds to an interval of the heartbeat, and a value obtained by dividing one minute by the interval of the heartbeat corresponds to a heart rate in one minute.

Here, the heartbeat becomes greater and quicker in accordance with increase in the heart rate. Therefore, in FIG. 17, if a time interval of peaks between the waveform R and the waveform T is set as Δt, and a difference of height of the peaks between the waveform R and the waveform T is set as a, it can be considered that there is relationship illustrated in the graph in FIG. 18 between Δt and a. Specifically, as illustrated in FIG. 18, in the case where the heart rate increases, because the heartbeat becomes greater, a becomes greater, and because a time period required for one-time heartbeat becomes shorter, Δt becomes smaller.

Figure 18:
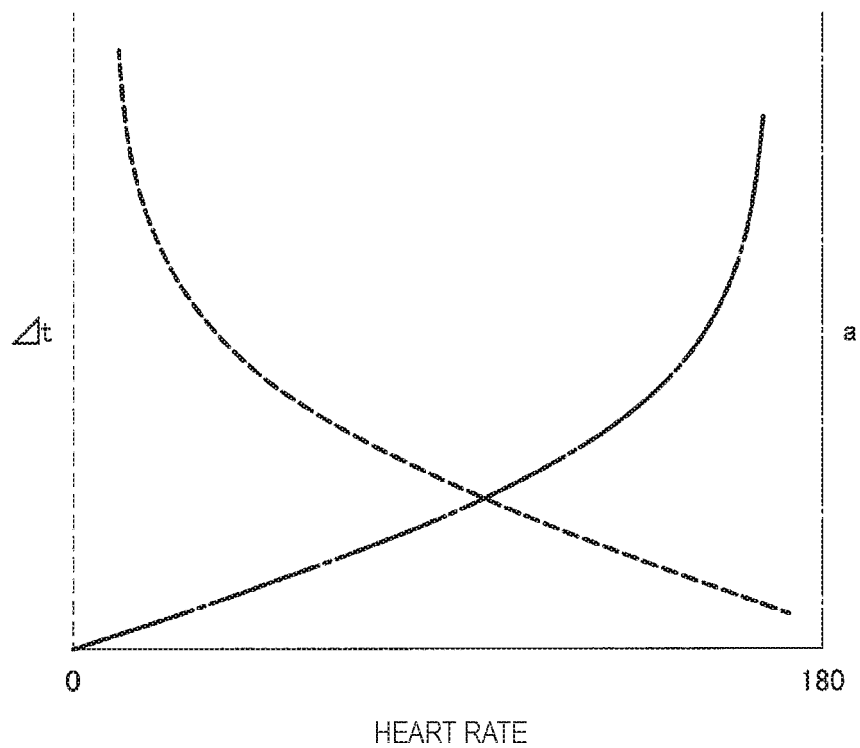
FIG. 18 is a graph schematically illustrating relationship between Δt and a illustrated in FIG. 17 and a heart rate.

Therefore, the reproduction control unit 326 can convey the heartbeat of the distributor to the user in an aspect which does not provide a less feeling of strangeness and which seems real by causing the reproducing unit 327 to vibrate on the basis of the relationship between the heart rate and Δt and a in the heartbeat, illustrated in FIG. 18.

Further, for example, in the case where the distributed information includes information regarding a timing of vibration, the reproduction control unit 326 may control reproduction of vibration by the reproducing unit 327 on the basis of the timing of the vibration. However, in the case where the vibration becomes unnatural as heartbeat if the reproduction control unit 326 causes the reproducing unit 327 to vibrate at the timing of vibration included in the distributed information, the reproduction control unit 326 may adjust the timing of vibration so that the vibration of the reproducing unit 327 becomes more natural.

For example, in the case where the reproduction control unit 326 changes the period of the vibration of the reproducing unit 327 in accordance with change of the heart rate of the distributor, there is a case where an interval between vibration after the period is changed and vibration immediately before the period is changed becomes extremely short. However, it is unnatural that the interval of the heartbeat is short only at one portion, in which case, the user has a sense of strangeness. Therefore, in the case where the reproduction control unit 326 changes the period of the vibration of the reproducing unit 327 on the basis of the distributed information, the reproduction control unit 326 may adjust the timing of the vibration of the reproducing unit 327 so that change of the period of the vibration becomes moderate.

Figure 19:
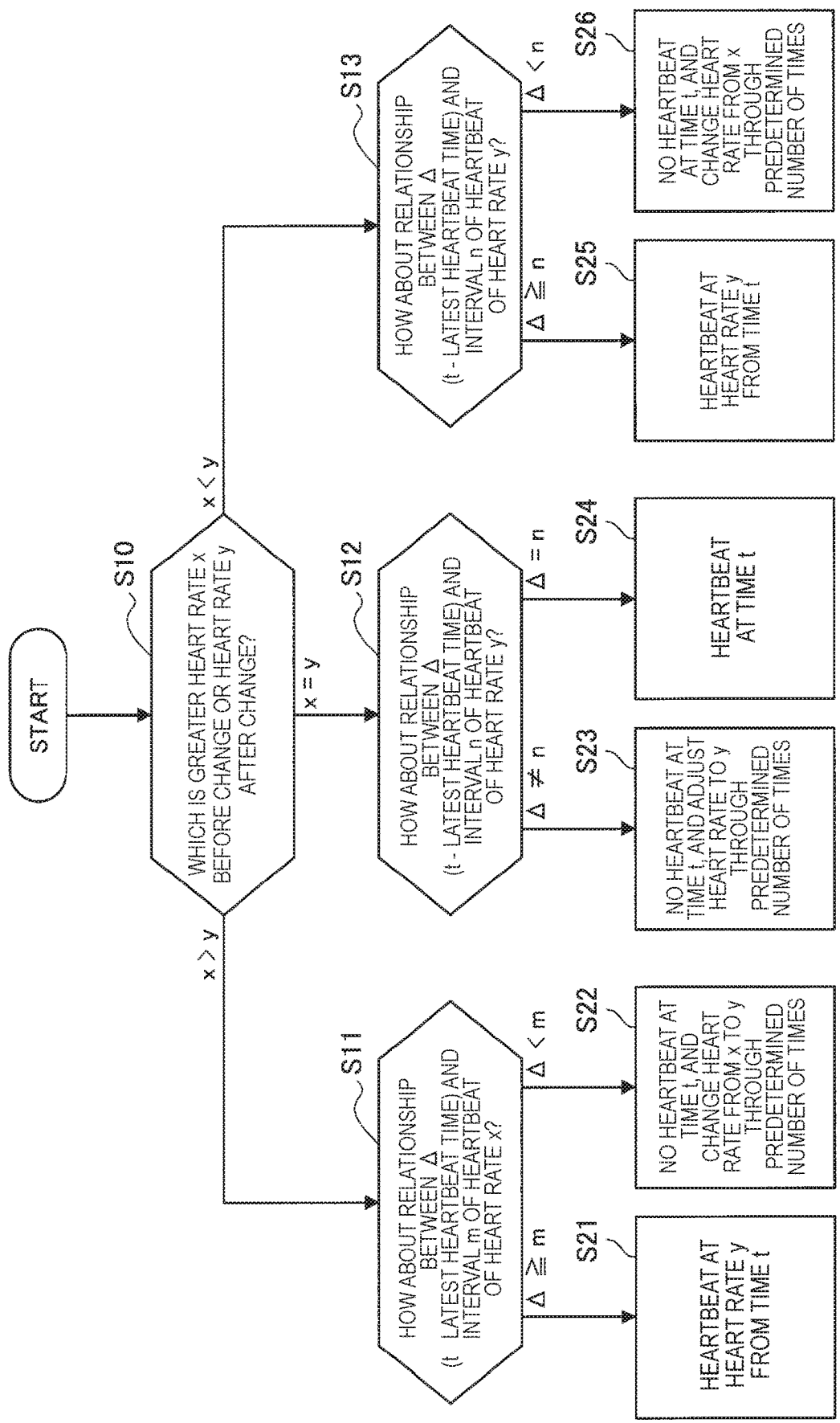
FIG. 19 is a flowchart explaining judgment in the case where vibration of the heart rate to be reproduced is changed.

Details of the above-described judgement by the reproduction control unit 326 will be described with reference to FIG. 19. FIG. 19 is a flowchart explaining judgement in the case where vibration of the heart rate to be reproduced at the reproducing unit 327 is changed.

It is assumed here that the distributed information is information which changes the period of the vibration by the reproducing unit 327 from a heart rate x (an interval of heartbeat is m) to a heart rate y (an interval of heartbeat is n) on the basis of the heart rate of the distributor. Further, t is time indicating the timing of vibration included in the distributed information.

As illustrated in FIG. 19, first, the reproduction control unit 326 judges which is greater the heart rate x before change or the heart rate y after change (S10).

For example, in the case where the heart rate x before change is greater than the heart rate y after change (that is, the heartbeat after change is slower) (x>y), the reproduction control unit 326 judges relationship between a difference Δ between the indicated vibration timing t and the last heartbeat time, and an interval m of heartbeat of the heart rate x before change (S11).

In the case where the difference Δ between the vibration timing t and the latest heartbeat time is equal to or greater than the interval m of the heartbeat before change (that is, the interval of the heartbeat is not shortened by change of the heart rate) (Δ≥m), the reproduction control unit 326 causes the reproducing unit 327 to vibrate at the indicated vibration timing t (S21). Meanwhile, in the case where the difference Δ between the vibration timing t and the latest heartbeat time becomes less than the interval m of the heartbeat before change (that is, the interval of the heartbeat is shortened by change of the heart rate) (Δ<m), the reproduction control unit 326 causes the reproducing unit 327 to vibrate at a timing delayed from the indicated vibration timing t. Thereafter, the reproduction control unit 326 gradually changes the heart rate from x to y through predetermined number of times (approximately three times) (S22).

Further, in S10, in the case where the heart rate x before change is the same as the heart rate y after change (that is, the heartbeat does not change before and after change) (x=y), the reproduction control unit 326 judges relationship between the difference Δ between the indicated vibration timing t and the latest heartbeat time, and an interval n of the heartbeat of the heart rate y after change (S12).

In the case where the difference Δ between the vibration timing t and the latest heartbeat time is not the same as the interval n of the heartbeat after change (that is, synchronization of the heartbeat is lost) (Δ≠m), the reproduction control unit 326 causes the reproducing unit 327 to vibrate at a timing different from the indicated vibration timing t. Thereafter, the reproduction control unit 326 gradually returns the heart rate to y through a predetermined number of times (approximately three times) (S23). Meanwhile, in the case where the difference Δ between the vibration timing t and the latest heartbeat time is the same as the interval n of the heartbeat after change (that is, synchronization of the heart rate is not lost) (Δ=m), the reproduction control unit 326 causes the reproducing unit 327 to vibrate at the indicated vibration timing t (S24).

Further, in S10, in the case where the heart rate x before change is less than the heart rate y after change (that is, the heartbeat after change is faster) (x<y), the reproduction control unit 326 judges relationship between a difference Δ between the indicated vibration timing t and the last heartbeat time, and an interval n of heartbeat of the heart rate y after change (S13).

In the case where the difference Δ between the vibration timing t and the latest heartbeat time is equal to or greater than the interval n of the heartbeat after change (that is, the interval of the heartbeat is not shortened by change of the heart rate) (Δ≥n), the reproduction control unit 326 causes the reproducing unit 327 to vibrate at the indicated vibration timing t (S25). Meanwhile, in the case where the difference Δ between the vibration timing t and the latest heartbeat time becomes less than the interval n of the heartbeat after change (that is, the interval of the heartbeat is shortened by change of the heart rate) (Δ<n), the reproduction control unit 326 causes the reproducing unit 327 to vibrate at a timing delayed from the indicated vibration timing t. Thereafter, the reproduction control unit 326 gradually changes the heart rate from x to y through predetermined number of times (approximately three times) (S26).

By the reproduction control unit 326 controlling the vibration of the reproducing unit 327 through such judgement, it is possible to convey the heartbeat of the distributor to the user in a natural aspect which does not provide a sense of strangeness.

Here, in the information processing system according to the present embodiment, in addition to the vibration information, the voice information of the distributor collected at the distribution terminal 32A may be included in the distributed information.

In such a case, the reproducing unit 327 may further include a voice output device such as a speaker and a headphone. In such a case, the reproduction terminal 32B can reproduce the voice information in addition to the vibration information.

Figure 20:
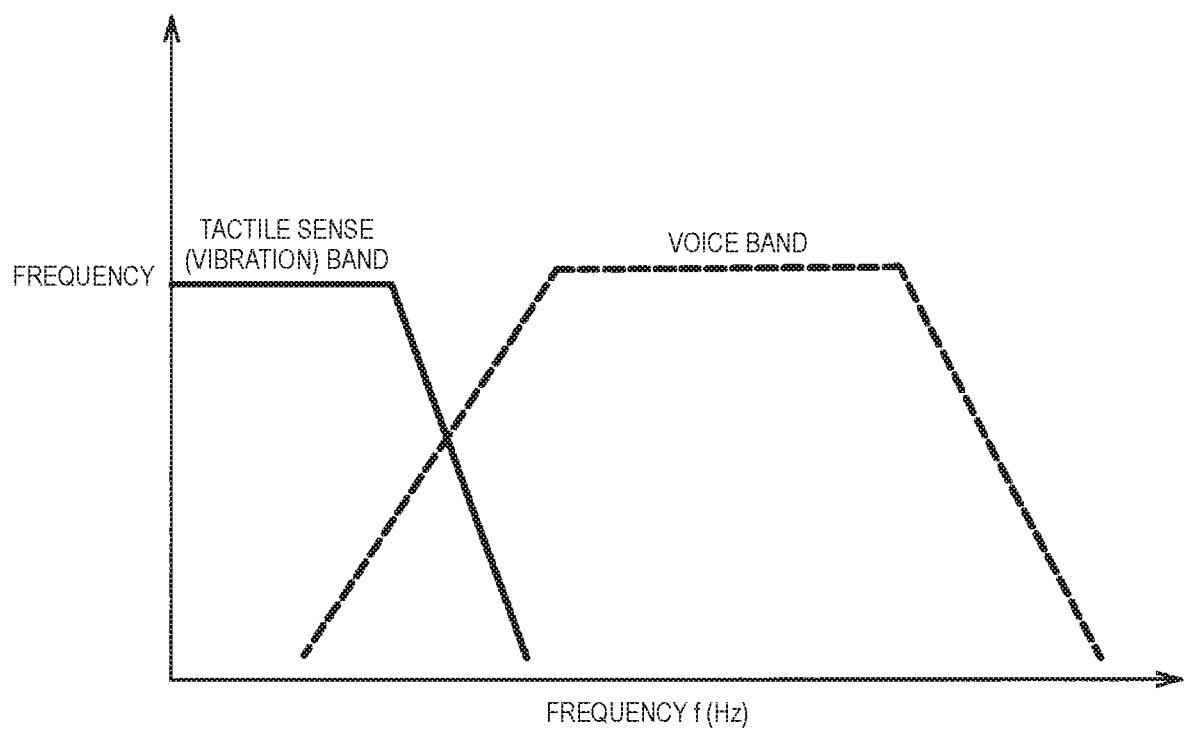
FIG. 20 is a graph schematically illustrating a frequency band of voice and a frequency band of vibration.

Further, the reproducing unit 327 may include an actuator which can reproduce both vibration and voice. This point will be described with reference to FIG. 20. FIG. 20 is a graph schematically illustrating a frequency band of voice and a frequency band of vibration.

Because the voice is vibration of air, the actuator which generates vibration can reproduce voice by vibrating air. However, as illustrated in FIG. 20, while the frequency band of voice is approximately 200 Hz to 40,000 Hz, the frequency band of vibration is approximately 0.1 Hz to 500 Hz, and the frequency bands are widely different from each other. Therefore, in the case where the reproducing unit 327 reproduces both vibration and voice with a single actuator, the reproducing unit 327 is constituted with a vibration actuator which can reproduce a wide frequency band, and which can reproduce both the frequency band of voice and the frequency band of vibration.

Here, there is a possibility that if the voice information included in the distributed information is reproduced with a speaker, or the like, the reproduced voice may be listened to by a person around the reproduction terminal, or the like. Meanwhile, in the case where the vibration information included in the distributed information is reproduced with the vibration actuator, the reproduced vibration is conveyed only to the user who wears the reproduction terminal 32B. Therefore, for example, in an environment where the voice information cannot be reproduced with the reproduction terminal 32B, the reproduction control unit 326 may control the reproducing unit 327 to reproduce only the vibration information included in the distributed information and not to reproduce the voice information.

Specifically, in the case where a state of the reproduction terminal 32B is set at a mute state (which is, so-called, a manner mode or a silent mode), the reproduction control unit 326 may control the reproducing unit 327 so as to reproduce only vibration information included in the distributed information and not to reproduce voice information. In such a case, the user can perceive the distributed information without other persons around the user knowing about the distributed information.

Further, in the case where the reproducing unit 327 reproduces both vibration and voice with a single actuator, the reproduction control unit 326 may control the reproducing unit 327 so as not to reproduce a frequency equal to or higher than a predetermined threshold (such as, for example, 300 Hz). Because the frequency of the voice is equal to or higher than approximately 300 Hz, and the frequency of the vibration is less than 300 Hz, by a frequency band of the distributed information to be reproduced being limited with such a threshold, the reproducing unit 327 can reproduce only the vibration information except the voice information.

According to such control, for example, in the case where the distributor transmits the distributed information during running, a statement of the distributor such as "I'm running now" is not reproduced, and only the heartbeat of the distributor and vibration by running are reproduced at the reproduction terminal 32B.

Figure 21:
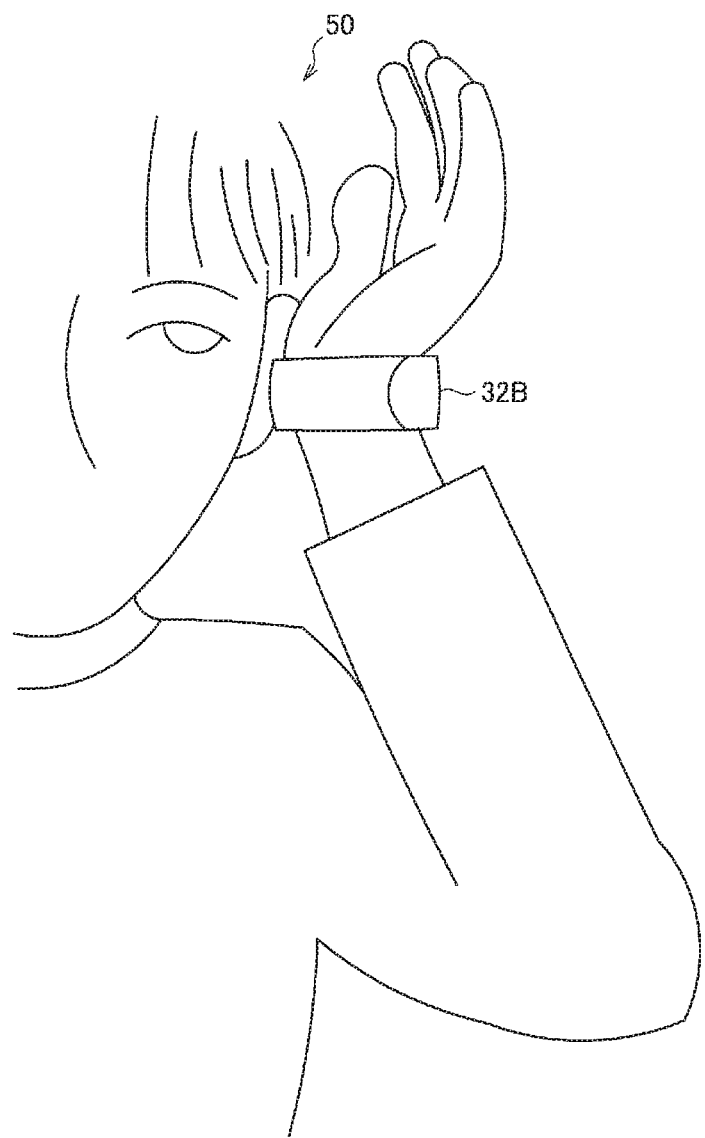
FIG. 21 is a schematic diagram illustrating an example of specific gesture action by a user.

Further, the reproduction control unit 326 may control reproduction of the voice information, a volume of the reproduction, or the like, on the basis of specific gesture action. This point will be described with reference to FIG. 21. FIG. 21 is a schematic diagram illustrating an example of the specific gesture action by the user.

Specifically, as illustrated in FIG. 21, in the case where the user 50 performs gesture action of bringing the reproduction terminal 32B close to his/her ear, the reproduction control unit 326 may reproduce the voice information at a volume smaller than normal. In such a case, the user can perceive both the voice information and the vibration information included in the distributed information without other persons around the user knowing about the voice information and the vibration information.

For example, at the reproduction terminal 32B whose state is set at the mute state, the reproduction control unit 326 may reproduce the voice information at a volume smaller than normal only in the case where the user 50 performs gesture action of bringing the reproduction terminal 32B close to his/her ear. Further, the reproduction control unit 326 may reproduce the voice information at a volume smaller than normal in the case where the user 50 performs gesture action of bringing the reproduction terminal 32B close to his/her ear, and may reproduce the voice information at a normal volume in other cases. Note that the reproduction control unit 326 may perform the above-described control in the case where it is detected that the reproduction terminal 32B approaches the user's ear regardless of the form of the reproduction terminal 32B illustrated in FIG. 21 and the gesture action.

Note that the gesture action by the user can be detected with a sensor such as a proximity sensor, an acceleration sensor and a gyro sensor provided at the reproduction terminal 32B. Further, while these kinds of reproduction control are performed on the voice information, the reproduction control as described above is not performed on the vibration information. For example, the vibration information may be reproduced at equal strength regardless of setting such as the mute state of the reproduction terminal 32B, the gesture action, or the like.

[2.3. Operation of Information Processing System]

Operation of the information processing system according to the present embodiment will be described next using specific examples with reference to FIG. 22 and FIG. 23. Operation examples of the information processing system according to the present embodiment described below are operation examples where, for example, the heartbeat of the distributor is distributed to the reproduction terminal 32B in coordination with performance (such as, for example, concert) by the distributor such as an idol.

(First Operation Example)

A first operation example of the information processing system according to the present embodiment will be described first with reference to FIG. 22. FIG. 22 is a sequence diagram illustrating the first operation example of the information processing system according to the present embodiment. Note that the first operation example is an operation example in the case where voice information of the performance is not distributed to the reproduction terminal 32B.

Figure 22:
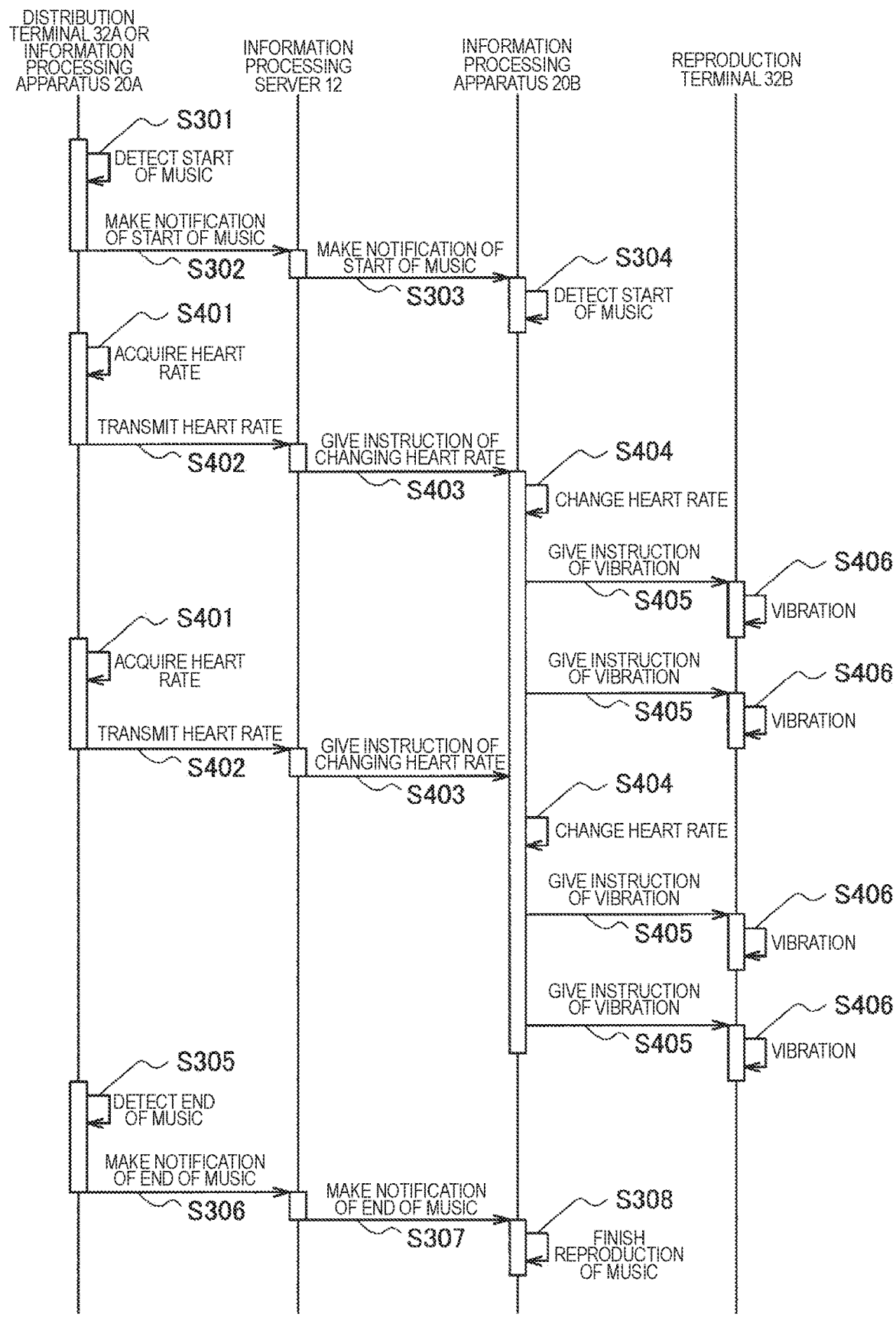
FIG. 22 is a sequence diagram illustrating a first operation example of the information processing system according to the second embodiment.

As illustrated in FIG. 22, first, in the case where start of music is detected at the distribution terminal 32A (S301), the distribution terminal 32A notifies the information processing server 12 of the start of the music (S302). Here, the start of the music may be automatically detected at the distribution terminal 32A or the information processing apparatus 20A or may be detected through input by the distributor, or the like. Then, the information processing server 12 notifies the information processing apparatus 20B of the start of the music (S303), and the information processing apparatus 20B starts reproduction of the music for which is a notification of the start is made (S304). Note that voice information of the music reproduced by the information processing apparatus 20B may be stored in the information processing apparatus 20B or may be stored in the information processing server 12, an external server, or the like.

Meanwhile, the distribution terminal 32A acquires information regarding the heart rate of the distributor (S401) and transmits the acquired information regarding the heart rate to the information processing server 12 (S402). Then, the information processing server 12 instructs the information processing apparatus 20B to change a heart rate to be reproduced (S403). The information processing apparatus 20B changes the heart rate to be reproduced at the reproduction terminal 32B (S404) and instructs the reproduction terminal 32B to vibrate on the basis of the changed heart rate (S405). By this means, the reproduction terminal 32B vibrates on the basis of the instruction of vibration from the information processing apparatus 20B (S406). Therefore, the information processing system can convey the heartbeat of the distributor to the user by repeating the above-described operation from S401 to S406 at a predetermined interval (such as, for example, every 5 seconds).

Further, in the case where end of the music is detected at the distribution terminal 32A (S305), the distribution terminal 32A notifies the information processing server 12 of the end of the music (S306). Note that the end of the music may be automatically detected at the distribution terminal 32A or the information processing apparatus 20A or may be detected through input by the distributor, or the like. Then, the information processing server 12 notifies the information processing apparatus 20B of the end of the music (S307), and the information processing apparatus 20B finishes reproduction of the music for which the notification is made (S308). In this event, in the case where reproduction is finished in the middle of the music, the information processing apparatus 20B may finishes the reproduction of the music through fade-out.

Here, in the case where start of the next music is detected at the distribution terminal 32A, the information processing system can distribute the heartbeat of the distributor to the reproduction terminal 32B in coordination with performance by the distributor by the processing returning to S301 and the above-described sequence being repeated. According to the information processing system according to the present embodiment, it is possible to cause the user who is not present at the venue to experience the performance by the distributor in a pseudo manner.

(Second Operation Example)

A second operation example of the information processing system according to the present embodiment will be described next with reference to FIG. 23. FIG. 23 is a sequence diagram illustrating the second operation example of the information processing system according to the present embodiment. Note that the second operation example is an operation example in the case where voice information of the performance is distributed to the reproduction terminal 32B.

Figure 23:
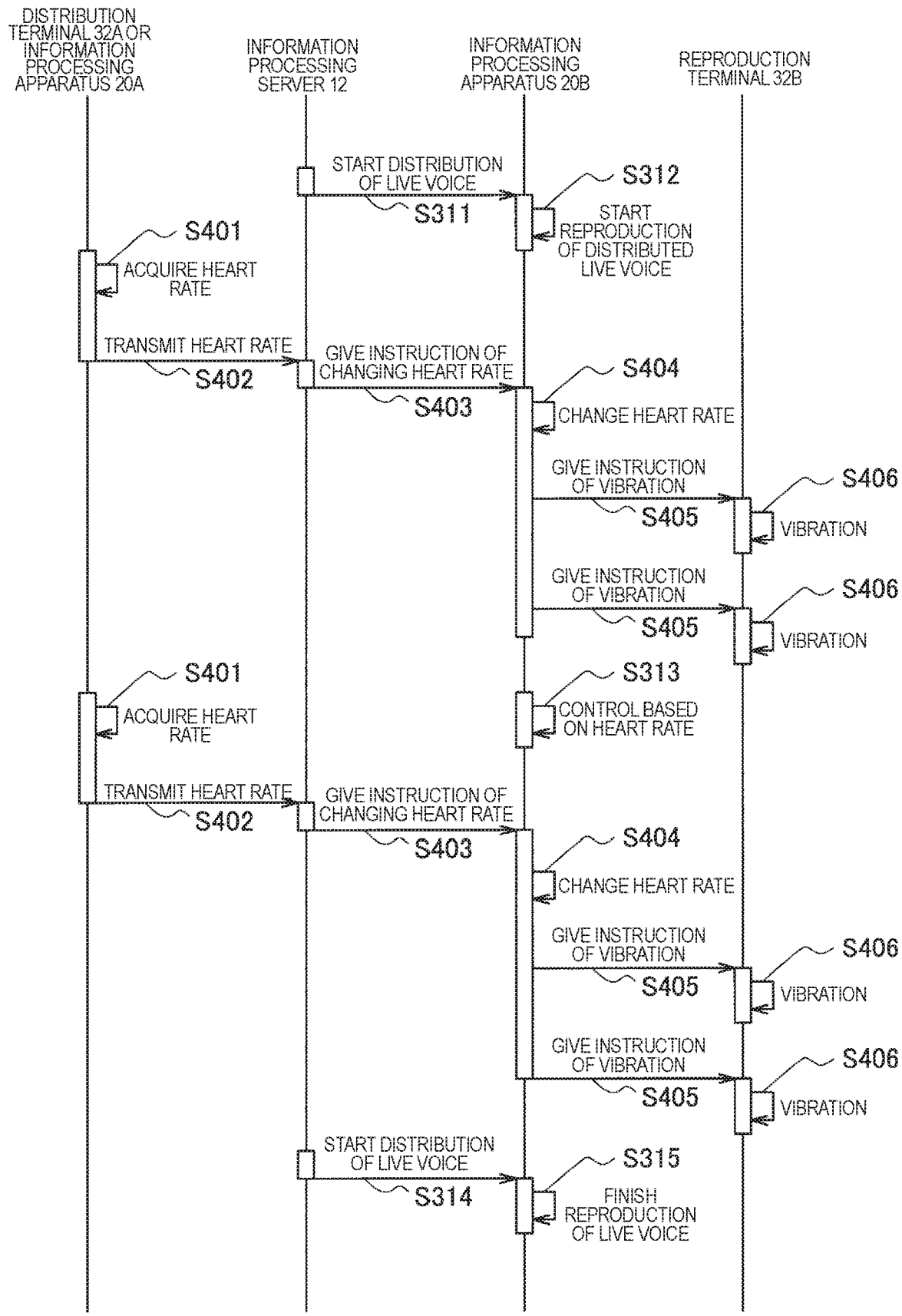
FIG. 23 is a sequence diagram illustrating a second operation example of the information processing system according to the second embodiment.

As illustrated in FIG. 23, first, distribution of live voice which is the performance of the distributor from the information processing server 12 is started (S311), and the information processing apparatus 20B starts reproduction of the distributed live voice (S312). The live voice may be voice collected at the distribution terminal 32A or may be voice collected at a microphone, or the like, provided at the venue where the performance is given.

Meanwhile, the distribution terminal 32A acquires information regarding the heart rate of the distributor (S401) and transmits the acquired information regarding the heart rate to the information processing server 12 (S402). Then, the information processing server 12 instructs the information processing apparatus 20B to change a heart rate to be reproduced (S403). The information processing apparatus 20B changes the heart rate to be reproduced at the reproduction terminal 32B (S404) and instructs the reproduction terminal 32B to vibrate on the basis of the changed heart rate (S405). By this means, the reproduction terminal 32B vibrates on the basis of the instruction of vibration from the information processing apparatus 20B (S406). Therefore, the information processing system can convey the heartbeat of the distributor to the user by repeating the above-described operation from S401 to S406 at a predetermined interval (such as, for example, every 5 seconds).

Further, in the case where distribution of the live voice from the information processing server 12 is finished (S314), the information processing apparatus 20B finishes the reproduction of the live voice (S315). Here, the information processing apparatus 20B may perform control based on the received heart rate of the distributor during reproduction of the live voice (S313). For example, the information processing apparatus 20B may perform control so that a volume of music to be reproduced becomes larger as the heart rate of the distributor becomes larger.

Note that, both in the above-described first operation example and second operation example, the information processing server 12 may transmit an image of a venue (such as, for example, a concert venue) where the distributor such as an idol gives performance, in addition to the distributed information to the information processing apparatus 20B or the reproduction terminal 32B at predetermined intervals (such as, for example, 30 seconds). According to this, the information processing system according to the present embodiment can cause the user who is not present at the venue of the performance to experience the performance by the distributor deeply in a pseudo manner.

Further, the information processing server 12 may distribute voice by the distributor in place of the heartbeat of the distributor to the reproduction terminal 32B as vibration information. For example, voice of singing of the distributor at the performance may be distributed to the reproduction terminal 32B, and may be reproduced at the reproduction terminal 32B as vibration. According to this, the information processing system according to the present embodiment can cause the user who is not present at the venue of the performance to experience the performance by the distributor deeply in a pseudo manner.

[2.4. Modified Examples]

While the information processing system according to the present embodiment has been described above, there can be various other modified examples for the information processing system according to the present embodiment as described below.

(Storage of Vibration Information in Medium)

The distributed information distributed in the information processing system according to the present embodiment can be caused to be stored in a storage medium, or the like. In such a case, the vibration information is stored in a channel provided separately from the voice information.

For example, it is also possible to create a format by changing one of channels such as a 5.1 channel format, in which voice can be stored, to a channel for storing the vibration information, and cause the distributed information to be stored in the storage medium using the format. According to such a configuration, by reproducing the distributed information stored in the storage medium, it is possible to experience the heartbeat or the tactile sense of the distributor along with the image and the voice of the performance of the distributer.

Further, in the case where there is a plurality of distributors, the information of the heartbeat or the tactile sense of each of the distributors may be stored in the storage medium along with voice information and image information of performance of the distributors. In such a case where the information stored in the storage medium is reproduced, for example, information regarding heartbeat or a tactile sense of a distributor who appears in the image information may be reproduced along with the image information, or information regarding heartbeat or a tactile sense of a distributor designated by the user may be reproduced.

(Coordination with Other Application)

The information processing system according to the present embodiment can perform operation in coordination with an external information processing server or an external application program (such as, for example, SNS).

For example, in the information processing system according to the present embodiment, the vibration in accordance with a text message of the distributor posted on an external SNS, or the like, may be transmitted to the reproduction terminal 32B. Specifically, an onomatopoetic word included in the text message of the distributor is extracted using an onomatopoetic database, and vibration information corresponding to the extracted onomatopoetic word may be transmitted to the reproduction terminal 32B. Further, by text analysis being performed on the text message of the distributor, feeling attribute (such as, for example, joy, anger, sorrow, pleasure, positive and negative) may be determined from the text message, and vibration information corresponding to the determined feeling attribute may be transmitted to the reproduction terminal 32B. Still further, vibration information in accordance with an amount of reaction to the text message of the distributor posted on an SNS, or the like, may be transmitted to the reproduction terminal 32B. According to this, the information processing system can make interaction between the distributor and the user more actively.

(Utilization of Distributed Information)

Further, the information processing system according to the present embodiment can offer service using the vibration information transmitted to the information processing apparatus 20B or the reproduction terminal 32B.

For example, in the information processing system according to the present embodiment, in coordination with reproduction of music at the information processing apparatus 20B, the vibration information corresponding to the music which is being reproduced may be reproduced at the reproduction terminal 32B. Further, the information processing apparatus 20B may convert voice information of the music which is being reproduced into vibration information and reproduce the converted vibration information at the reproduction terminal 32B. Further, in the case where the reproduction terminal 32B or the information processing apparatus 20B includes a function as a clock, the reproduction terminal 32B may reproduce the transmitted distributed information as alarm for notification of time. Further, in the case where the information processing apparatus 20B receives an email, a notification, an incoming call, or the like, the reproduction terminal 32B may reproduce the transmitted distributed information as alarm for notification of receipt of the email, the notification or the incoming call. In this case, the reproduction terminal 32B may change the distributed information to be reproduced for each type of the email, the notification, the incoming call, or the like. According to this, the user can utilize the transmitted distributed information in various manners.

(Utilization at Performance)

Further, the information processing system according to the present embodiment can be used for interaction between the distributor (an idol or an artist) and the user (fan) upon performance, or the like, such as a concert and a live. According to this, the information processing system can make interaction with the user more actively.

Specifically, in the case where the reproduction terminal 32B can recognize gesture action, at the reproduction terminal 32B, reproduction of voice information or vibration information may be controlled on the basis of whether or not specific gesture action is performed. For example, the reproduction terminal 32B may be controlled so that the voice information or the vibration information is reproduced only in the case where action of shaking the head (which is also referred to as "head-banging") is performed. Further, the reproduction terminal 32B may be controlled so that a reproduction volume of the voice information becomes greater as a degree of the action of shaking the head (such as a frequency and a degree of action of shaking the head) becomes greater. Still further, at a site of the performance, the reproduction terminal 32B may measure degrees of action of shaking the head and may be controlled so as to change the distributed information or content (such as the number of songs for an encore) of the performance on the basis of an integrated value of the measured degrees.

Further, at the site of the performance, the distributed information such as specific vibration and voice may be transmitted to the reproduction terminal 32B in accordance with respective regions within the site. For example, in the information processing system according to the present embodiment, control may be performed so that the distributed information including specific vibration is transmitted to the reproduction terminal 32B located at a region which is pointed by the distributor at the site of the performance. Note that, while action of pointing by the distributor may be detected at, for example, the distribution terminal 32A, the action may be detected using other methods such as image recognition.

Further, in the information processing system according to the present embodiment, control may be performed so that special distributed information is transmitted to the reproduction terminal 32B only in a limited predetermined period before performance. For example, the information processing system may be controlled so that voice information or vibration information of regular life of the distributor is transmitted to the reproduction terminal 32B only in a limited predetermined period.

(Modified Examples of Distributed Information)

While, in the above description, the distributed information distributed in the information processing system according to the present embodiment is set as information depending on physicality of the distributor such as vibration information which conveys a tactile sense or heartbeat, the technology according to the present disclosure is not limited to the above-described examples. For example, the distributed information distributed in the information processing system according to the present embodiment may be content information including various kinds of content such as music, an image, a moving image and text.

3. Hardware Configuration of Information Processing Server

Subsequently, a hardware configuration of the information processing server 10 according to each embodiment of the present disclosure will be described with reference to FIG. 24. FIG. 24 is a block diagram illustrating an example of the hardware configuration of the information processing server 10 according to each embodiment of the present disclosure. Note that information processing to be executed by the information processing server 10 is implemented through cooperation between software and hardware.

As shown in FIG. 24, the information processing server 10 includes, for example, a central processing unit (CPU) 601, a read only memory (ROM) 603, a random access memory (RAM) 605, a bridge 611, internal buses 607 and 609, an interface 613, an input device 615, an output device 617, a storage device 619, a drive 621, a connection port 623, and a communication device 625.

The CPU 601 functions as an arithmetic processing unit and a control device and controls the whole operation of the information processing server 10 in accordance with programs stored on the ROM 603 or the like. The ROM 603 stores the programs and operation parameters used by the CPU 601, and the RAM 605 temporarily stores programs used in execution of the CPU 601, parameters appropriately changed in execution thereof, and the like. The CPU 601 may function as, for example, a distributed information receiving unit 120, a distribution control unit 140, a distributed information transmitting unit 150, a response providing unit 160 and a response conveying unit 170.

Those CPU 601, ROM 603, and RAM 605 are mutually connected via the bridge 611, the internal buses 607 and 609, and the like. Further, the CPU 601, the ROM 603, and the RAM 605 are also connected to the input device 615, the output device 617, the storage device 619, the drive 621, the connection port 623, and the communication device 625 via the interface 613.

The input device 615 is made up of, for example, an input device to which information is input, such as a touchscreen, a keyboard, a button, a microphone, a switch, or a lever, and an input control circuit for generating an input signal on the basis of input from a user and outputting the input signal to the CPU 601.

The output device 617 includes, for example, a display device such as a liquid crystal display device, an organic EL display device, and a lamp and an audio output device such as a loudspeaker and headphones. For example, the display device displays a generated image, and the audio output device converts audio data or the like into audio and outputs the audio.

The storage device 619 is a data storage device configured as an example of the storage unit of the information processing server 10. The storage device 619 may include a storage medium, a storage device for storing data on the storage medium, a reading device for reading the data from the storage medium, and a deleting device for deleting the stored data. For example, the storage device 619 may function as the distributed information storage unit 130.

The drive 621 is a reader/writer for a storage medium. The drive 621 reads information stored on a removable storage medium inserted into the drive 621, such as various optical disc, a semiconductor memory or the like, and outputs the information to the RAM 605. Further, the drive 621 can write information into the removable storage medium.

The connection port 623 is, for example, a connection interface configured as a connection port for connecting an external connection device, such as a USB port or an optical audio terminal.

The communication device 625 is, for example, a communication interface configured as a communication device or the like to be connected to a network 40. Further, the communication device 625 may be a communication device compatible with a wired or wireless LAN or a cable communication device for performing wired cable communication. The communication device 625 may function as the network connecting unit 110.

4. CONCLUSION

As described above, according to the information processing system according to each embodiment of the present disclosure, it is possible to provide a system which distributes distributed information to a user and which has a response to the distributed information provided from the user. According to this, the information processing system can cause the user to whom the distributed information is distributed to have a stronger feeling and can shorten a psychological distance between a distributor and the user.

Further, in the hardware such as the CPU, the ROM, and the RAM, it is also possible to prepare a computer program for causing another information processing server to exert functions equal to configurations forming the above-mentioned information processing server according to the first or second embodiment of the present disclosure. Further, a storage medium on which the computer program is stored is also provided.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)
A reproduction terminal including:
a reproducing unit configured to reproduce distributed information;
a sensor unit configured to detect body action of a user; and
a control unit configured to process operation regarding provision of a response to the distributed information on the basis of the body action detected at the sensor unit.

(2)
The reproduction terminal according to (1),
in which the distributed information is voice information uttered by a distributor.

(3)
The reproduction terminal according to (1) or (2),
in which the response includes evaluation to the distributed information.

(4)
The reproduction terminal according to any one of (1) to (3),
in which the response includes voice information uttered by the user in response to the distributed information.

(5)
The reproduction terminal according to (3) or (4),
in which the response further includes information regarding a location of the reproduction terminal.

(6)
The reproduction terminal according to any one of (1) to (5), further including:
a guide voice control unit configured to control output of guide voice information which notifies the user that the distributed information is distributed.

(7)
The reproduction terminal according to (6),
in which the distributed information is distributed from a plurality of distributors, and
the guide voice information is voice information uttered by a distributor designated by the user among the plurality of distributors.

(8)
The reproduction terminal according to (7),
in which the guide voice control unit controls the guide voice information so that a distributor who distributes the distributed information is different from a distributor who utters the guide voice information.

(9)
The reproduction terminal according to any one of (1) to (8),
in which the reproduction terminal is worn on a body of a user, and
the reproducing unit controls reproduction of the distributed information on the basis of whether the reproduction terminal is worn.

(10)
The reproduction terminal according to (9),
in which the sensor unit detects whether the reproduction terminal is worn.

(11)
The reproduction terminal according to (10),
in which the reproduction terminal is worn on a head of the user, and
the sensor unit detects motion of the head of the user.

(12)
The reproduction terminal according to (1),
in which the distributed information is vibration information which conveys a tactile sense or heartbeat of a distributor.

(13)
The reproduction terminal according to (12),
in which the vibration information includes information regarding a heart rate of the distributor, and information regarding a timing for starting vibration at the heart rate.

(14)
The reproduction terminal according to (13),
in which the vibration information is distributed with a predetermined period.

(15)
The reproduction terminal according to any one of (12) to (14),
in which the distributed information further includes voice information uttered by the distributor in addition to the vibration information.

(16)
The reproduction terminal according to (15),
in which, in a case where a state of the reproduction terminal is set at a mute state, the reproducing unit causes only the vibration information to be reproduced.

(17)
The reproduction terminal according to (16),
in which, in a case where it is detected by the sensor unit that the reproduction terminal approaches an ear of the user, the reproducing unit causes the voice information to be reproduced.

(18)
The reproduction terminal according to any one of (15) to (17),
in which the vibration information and the voice information are reproduced by a same actuator.

(19)
The reproduction terminal according to any one of (15) to (18),
in which, in a case where the distributor is giving performance, the distributed information includes the voice information of the distributor who is giving performance, or the voice information of the distributor corresponding to the performance, and the vibration information of the distributor in synchronization with the voice information.

(20)
A reproduction method including:
reproducing distributed information;
detecting body action of a user; and
processing operation regarding provision of a response to the distributed information on the basis of the detected body action by an arithmetic processing unit.

REFERENCE SIGNS LIST

10, 12 information processing server
20A information processing apparatus
20B information processing apparatus
30A, 32A distribution terminal
30B, 32B reproduction terminal
40 network
110 network connecting unit
120 distributed information receiving unit
130 distributed information storage unit
140 distribution control unit
150 distributed information transmitting unit
160 response providing unit 161 voice recognizing unit
162 error word processing unit
163 error word storage unit
170 response conveying unit
181 terminal managing unit
182 function restricting unit
311 communication unit
312 control unit
313 voice reproducing unit
314 distributed information acquiring unit
315 microphone unit
321 communication unit
322 control unit
323 voice reproducing unit
324 guide voice control unit
325 sensor unit
326 reproduction control unit
327 reproducing unit

The invention claimed is:

1. A reproduction terminal comprising:
a reproducing unit configured to reproduce distributed information;
a sensor unit configured to detect body action of a user; and
processing circuitry configured to process operation regarding provision of a response to the distributed information on a basis of the body action detected at the sensor unit, wherein
the distributed information includes vibration information which conveys a tactile sense or heartbeat of a distributor,
the distributed information further includes voice information uttered by the distributor in addition to the vibration information, and
in a case where the distributor is giving performance, the distributed information includes the voice information of the distributor who is giving performance, or the voice information of the distributor corresponding to the performance, and the vibration information of the distributor in synchronization with the voice information.

2. The reproduction terminal according to claim 1, wherein the distributed information is voice information uttered by a distributor.

3. The reproduction terminal according to claim 1, wherein the response includes evaluation to the distributed information.

4. The reproduction terminal according to claim 3, wherein the response further includes information regarding a location of the reproduction terminal.

5. The reproduction terminal according to claim 1, wherein the response includes voice information uttered by the user in response to the distributed information.

6. The reproduction terminal according to claim 1, further comprising:
a guide voice control circuit configured to control output of guide voice information which notifies the user that the distributed information is distributed.

7. The reproduction terminal according to claim 6, wherein the distributed information is distributed from a plurality of distributors, and
the guide voice information is voice information uttered by a distributor designated by the user among the plurality of distributors.

8. The reproduction terminal according to claim 7, wherein the guide voice control circuit controls the guide voice information so that a distributor who distributes the distributed information is different from a distributor who utters the guide voice information.

9. The reproduction terminal according to claim 1, wherein the reproduction terminal is worn on a body of a user, and
the reproducing unit controls reproduction of the distributed information on a basis of whether the reproduction terminal is worn.

10. The reproduction terminal according to claim 9, wherein the sensor unit detects whether the reproduction terminal is worn.

11. The reproduction terminal according to claim 10, wherein the reproduction terminal is worn on a head of the user, and
the sensor unit detects motion of the head of the user.

12. The reproduction terminal according to claim 1, wherein the vibration information includes information regarding a heart rate of the distributor, and information regarding a timing for starting vibration at the heart rate.

13. The reproduction terminal according to claim 12, wherein the vibration information is distributed with a predetermined period.

14. The reproduction terminal according to claim 1, wherein, in a case where a state of the reproduction terminal is set at a mute state, the reproducing unit causes only the vibration information to be reproduced.

15. The reproduction terminal according to claim 14, wherein, in a case where it is detected by the sensor unit that the reproduction terminal approaches an ear of the user, the reproducing unit causes the voice information to be reproduced.

16. The reproduction terminal according to claim 1, wherein the vibration information and the voice information are reproduced by a same actuator.

17. A reproduction method comprising:
reproducing distributed information;
detecting body action of a user; and
processing, using processing circuitry, operation regarding provision of a response to the distributed information on a basis of the detected body action, wherein
the distributed information includes vibration information which conveys a tactile sense or heartbeat of a distributor,
the distributed information further includes voice information uttered by the distributor in addition to the vibration information, and
in a case where the distributor is giving performance, the distributed information includes the voice information of the distributor who is giving performance, or the voice information of the distributor corresponding to the performance, and the vibration information of the distributor in synchronization with the voice information.

* * * * *